US008008232B2

(12) United States Patent
Gewehr et al.

(10) Patent No.: US 8,008,232 B2
(45) Date of Patent: Aug. 30, 2011

(54) PYRAZOLECARBOXANILIDES, PROCESS FOR THEIR PREPARATION AND COMPOSITIONS COMPRISING THEM FOR CONTROLLING HARMFUL FUNGI

(75) Inventors: Markus Gewehr, Kastellaun (DE); Jochen Dietz, Mannheim (DE); Thomas Grote, Wachenheim (DE); Carsten Blettner, Hong Kong (CN); Wassilios Grammenos, Ludwigshafen (DE); Udo Hünger, Mannheim (DE); Bernd Müller, Frankenthal (DE); Frank Schieweck, Heβheim (DE); Anja Schwögler, Mannheim (DE); Jan Klaas Lohmann, Mannheim (DE); Joachim Rheinheimer, Ludwigshafen (DE); Peter Schäfer, Ottersheim (DE); Siegfried Strathmann, Limburgerhof (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 668 days.

(21) Appl. No.: 11/883,957

(22) PCT Filed: Feb. 15, 2006

(86) PCT No.: PCT/EP2006/050962
§ 371 (c)(1),
(2), (4) Date: Aug. 8, 2007

(87) PCT Pub. No.: WO2006/087343
PCT Pub. Date: Aug. 24, 2006

(65) Prior Publication Data
US 2008/0153707 A1 Jun. 26, 2008

(30) Foreign Application Priority Data
Feb. 16, 2005 (DE) .................... 10 2005 007 160

(51) Int. Cl.
*A01N 43/56* (2006.01)
*C07D 231/10* (2006.01)

(52) U.S. Cl. .................. 504/280; 548/373.1; 548/374.1; 504/100; 504/101; 504/261

(58) Field of Classification Search ............... 548/356.1, 548/373.1, 374.1; 504/100, 101, 261, 280
See application file for complete search history.

(56) References Cited

U.S. PATENT DOCUMENTS

| 6,369,093 B1* | 4/2002 | Elbe et al. .............. 514/406 |
| 7,173,055 B1* | 2/2007 | Walter ..................... 514/406 |
| 7,329,633 B2* | 2/2008 | Dunkel et al. ............. 504/280 |
| 7,501,383 B2* | 3/2009 | Tormo I Blasco et al. ... 504/100 |
| 7,521,397 B2* | 4/2009 | Dunkel et al. ............. 504/280 |
| 7,598,206 B2* | 10/2009 | Gewehr et al. ............ 504/100 |
| 7,799,334 B2* | 9/2010 | Gewehr et al. ............ 424/405 |

FOREIGN PATENT DOCUMENTS

| EP | 0 455 058 A2 | 11/1991 |
| JP | 2001-302605 A | 10/2001 |
| WO | WO 98/35967 A2 | 8/1998 |
| WO | WO-00/14071 A2 | 3/2000 |
| WO | WO 03/066609 A1 | 8/2003 |
| WO | WO 03/099803 A1 | 12/2003 |
| WO | WO-2004/103975 A | 12/2004 |
| WO | WO-2005/023689 A1 | 12/2005 |
| WO | WO-2005/123690 A | 12/2005 |

OTHER PUBLICATIONS

Gewehr et al (2005): STN International HCAPLUS database, Columbus (OH), accession No. 2005: 1350318.*
Gewehr et al (2005): STN International HCAPLUS database, Columbus (OH), accession No. 2005: 1355575.*
Dunkel et al (2004): STN International HCAPLUS database, Columbus (OH), accession No. 2004: 1037078.*
Franek, M. et al., J. Argic Food Chem., 1992, 40(9), pp. 1559-1565.
Taniguchi K. et al. Chem Pharm Bull. 1992, (40)(1), pp. 240-244.

* cited by examiner

*Primary Examiner* — Golam M Shameem
(74) *Attorney, Agent, or Firm* — Birch, Stewart, Kolasch & Birch, LLP

(57) ABSTRACT

The present invention relates to pyrazolecarboxanilides I in which the variables are as defined below:
n is zero or 2;
m is 2 or 3;
$X^1$ is fluorine or chlorine;
$X^2$ is halogen;
Y is CN, $NO_2$, $C_1$-$C_4$-alkyl, $C_1$-$C_4$-haloalkyl, methoxy or methylthio;
p is zero or 1;
$R^1$ is fluorine, chlorine, bromine, $C_1$-$C_4$-alkyl or $C_1$-$C_4$-haloalkyl;
$R^2$ is hydrogen or halogen;
$R^3$ is hydrogen, methyl or ethyl;
W is O or S;
with the proviso that, if
a) W=O, $R^1$=methyl and $R^3$ is hydrogen, $R^2$ is not fluorine, or
b) W=O, n=0, m=2, p=0, $R^2$ and $R^3$ are hydrogen, $R^1$ is not trifluoromethyl or difluoromethyl,
to processes for preparing these compounds, to compositions comprising them and to methods for using them for controlling harmful fungi.

9 Claims, No Drawings

PYRAZOLECARBOXANILIDES, PROCESS FOR THEIR PREPARATION AND COMPOSITIONS COMPRISING THEM FOR CONTROLLING HARMFUL FUNGI

The present invention relates to pyrazolecarboxanilides of the formula I in which the variables are as defined below:
n is zero or 2;
m is 2 or 3;
$X^1$ is fluorine or chlorine;
$X^2$ is halogen;
Y is CN, $NO_2$, $C_1$-$C_4$-alkyl, $C_1$-$C_4$-haloalkyl, methoxy or methylthio;
p is zero or 1;
$R^1$ is fluorine, chlorine, bromine, $C_1$-$C_4$-alkyl or $C_1$-$C_4$-haloalkyl;
$R^2$ is hydrogen or halogen;
$R^3$ is hydrogen, methyl or ethyl;
W is O or S;
with the proviso that, if
a) W=O, $R^1$=methyl and $R^3$ is hydrogen, $R^2$ is not F, or
b) W=O, n=0, m=2, p=0, $R^2$ and $R^3$ are hydrogen, $R^1$ is not trifluoromethyl or difluoromethyl.

Here, in the case of multiple substitution, the substituents $X_1$ and $X_2$ may independently of one another have different meanings.

Moreover, the invention relates to processes for preparing these compounds, to compositions comprising them and to methods for their use for controlling harmful fungi, in particular *Botrytis*.

Pyrazolecarboxanilides having fungicidal action are known from the literature. Thus, for example, EP-A 545.099 and EP-A 589 301 describe biphenylanilides of this type which are monosubstituted at the biphenyl group.

WO 00/14071 describes specific 1,3-dimethyl-5-fluoropyrazolecarboxanilides and their fungicidal action.

Pyrazolecarboxanilides having a specific triple substitution at the biphenyl group are known from WO 03/070705 and JP-A 2001/302605.

WO 2004/103975 provides inter alia iodopyrazolecarboxanilides which differ from the present compounds I in particular in that they have an iodine substituent instead of $R^1$.

It was an object of the present invention to provide pyrazolecarboxanilides whose fungicidal action is better than that of the compounds of the prior art.

We have found that this object is achieved by the compounds I defined at the outset. Moreover, we have found processes for preparing these compounds, compositions comprising them and methods for their use for controlling harmful fungi.

Compared to the known compounds, the compounds of the formula I are more effective against harmful fungi.

The compounds of the formula I can be present in different crystal modifications whose biological activity may differ. They also form part of the subject matter of the present invention.

In the formula I, halogen is fluorine, chlorine, bromine or iodine, preferably fluorine or chlorine;

$C_1$-$C_4$-alkyl is methyl, ethyl, n-propyl, 1-methylethyl, n-butyl, 1-methylpropyl, 2-methylpropyl or 1,1-dimethylethyl, preferably methyl or ethyl;

$C_1$-$C_4$-haloalkyl is a partially or fully halogenated $C_1$-$C_4$-alkyl radical, where the halogen atom(s) is/are in particular fluorine and/or chlorine, i.e., for example, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2-chloro-2-fluoroethyl, 2,2,2-trifluoroethyl, 2-chloro-1,1,2-trifluoroethyl, 2-chloro-2,2-difluoroethyl, 2-bromo-2,2-difluoroethyl, 2,2-dichloro-2-fluoroethyl, 2,2,2-trichloroethyl, 1,1,2,2-tetrafluoroethyl, 1,1,2,2-tetrachloroethyl, pentafluoroethyl, 2,2,3,3-tetrafluoro-1-propyl, 1,1,2,3,3,3-hexafluoro-1-propyl, 1,1,1,3,3,3-hexafluoro-2-propyl, heptafluoro-1-propyl, heptafluoro-2-propyl, 2,2,3,3,4,4,4-heptafluoro-1-butyl or nonafluoro-1-butyl, in particular halomethyl, with particular preference $CH_2$—Cl, $CH(Cl)_2$, $CH_2$—F, $CH(F)_2$, $CF_3$, $CHFCl$, $CF_2Cl$ or $CF(Cl)_2$.

The compounds I are generally obtained by reacting a carbonyl halide of the formula II in a manner known per se (for example J. March, Advanced Organic Chemistry, 2nd Ed., 382 f, McGraw-Hill, 1977) in the presence of a base with an aniline of the formula III:

In the formula II, the radical Hal denotes a halogen atom, such as fluorine, chlorine, bromine and iodine, in particular fluorine, chlorine or bromine. This reaction is usually carried out at temperatures of from −20° C. to 100° C., preferably from 0° C. to 50° C.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also methylene chloride, dimethyl sulfoxide and dimethylformamide, particularly preferably toluene, methylene chloride and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and also alkali metal bicarbonates, such as sodium bicarbonate, and organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide and dimethoxymagensium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines.

Particular preference is given to using triethylamine and pyridine.

The bases are generally employed in equimolar amounts, based on the compound II. However, they can also be used in an excess of from 5 mol % to 30 mol %, preferably from 5 mol % to 10 mol %, or—if tertiary amines are used—if appropriate, as solvents.

The starting materials are generally reacted with one another in equimolar amounts. In terms of yield, it may be advantageous to employ II in an excess of from 1 mol % to 20 mol %, preferably from 1 mol % to 10 mol %, based on III.

The starting materials of the formulae II and III required for preparing the compounds I are known or can be synthesized analogously to known compounds (Helv. Chim. Acta, 60, 978 (1977); Zh. Org. Khim., 26, 1527 (1990); Heterocycles 26, 1885 (1987); Izv. Akad. Nauk. SSSR Ser. Khim., 2160 (1982); THL 28, 593 (1987); THL 29, 5463 (1988)).

Furthermore, it has been found that compounds of the formula I are obtained by reacting, in a known manner, carboxylic acids of the formula IV with an aniline of the formula III in the presence of dehydrating agents and, if appropriate, an organic base.

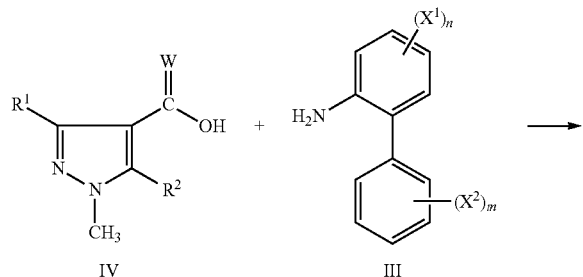

-continued

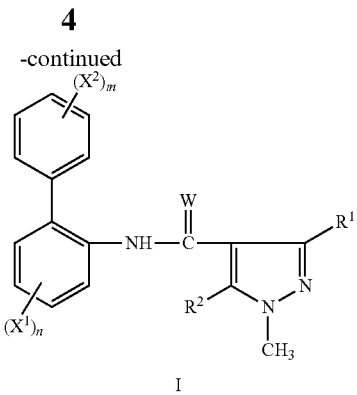

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide and dimethylformamide, particularly preferably methylene chloride, toluene and tetrahydrofuran.

It is also possible to use mixtures of the solvents mentioned.

Suitable dehydrating agents are 1,1'-carbonyldiimidazole, bis(2-oxo-3-oxazolidinyl)-phosphoryl chloride, carbodiimides, such as N,N'-dicyclohexylcarbodiimide, N-(3-dimethylaminopropyl)-N'-ethylcarbodiimide, phosphonium salts, such as (benzotriazol-1-yloxy)tris(dimethylamino)phosphonium hexafluorophosphate, bromotripyrrolidinophosphonium hexafluorophosphate, bromotris(dimethylamino)phosphonium hexafluorophosphate, chlorotripyrrolidinophosphonium hexafluorophosphate, uronium and thiuronium salts, such as O-(benzotriazol-1-yl)-N,N,N',N'-tetramethyluronium hexafluorophosphate, O-(7-azabenzotriazol-1-yl)-N,N, N',N'-tetramethyluronium hexafluorophosphate, S-(1-oxido-2-pyridyl)-N,N, N',N'-tetramethylthiuronium tetrafluoroborate, O-(2-oxo-1(2H)pyridyl)-N,N, N',N'-tetramethyluronium tetrafluoroborate, O-[(ethoxycarbonyl)cyanomethylenamino]-N,N,N',N'-tetramethyluronium tetrafluoroborate, carbenium salts, such as (benzotriazol-1-yloxy)dipyrrolidinocarbenium hexafluorophosphate, (benzotriazol-1-yloxy)dipiperidinocarbenium hexafluorophosphate, O-(3,4-dihydro-4-oxo-1,2,3-benzotriazin-3-yl)-N,N, N',N'-tetramethyluronium tetrafluoroborate, chloro-N',N'-bis(tetramethylene)formamidinium tetrafluoroborate, chlorodipyrrolidinocarbenium hexafluorophosphate, chloro-N,N,N',N'-bis(pentamethylene)-formamidinium tetrafluoroborate, imidazolium salts, such as 2-chloro-1,3-dimethylimidazolidinium tetrafluoroborate, preferably 1,1'-carbonyldiimidazole, bis(2-oxo-3-oxazolidinyl)phosphoryl chloride, N,N'-dicyclohexylcarbodiimide and N-(3-dimethyl-aminopropyl)-N'-ethylcarbodiimide.

Suitable organic bases are tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to using triethylamine and pyridine. The bases are generally employed in an excess of from 10 mol % to 200 mol %, preferably from 50 mol % to 150 mol %, based on the compound IV.

The starting materials are generally reacted with one another in equimolar amounts. In terms of yield, it may be advantageous to use an excess of from 1 mol % to 20 mol %, preferably from 1 mol % to 10 mol %, of one of the compounds. The dehydrating agents are generally employed in an excess of from 5 mol % to 100 mol %, preferably from 5 mol % to 60 mol %.

The starting materials of the formulae III and IV required for preparing the compounds I are known or can be synthesized analogously to the known compounds.

Compounds of the formula I where $R^3$=methyl or ethyl can be obtained by reacting compounds of the formula I where $R^3$=H in a manner known per se in the presence of a base with an alkylating agent:

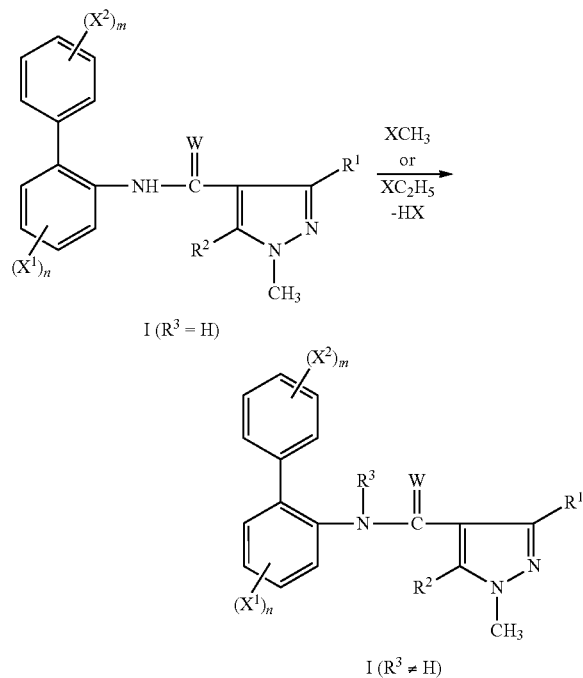

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, and also dimethyl sulfoxide and dimethylformamide, particularly preferably diethyl ether, tert-butyl methyl ether, tetrahydrofuran and dimethylformamide.

It is also possible to use mixtures of the solvents mentioned.

Suitable alkylating agents ($XCH_3$ or $XC_2H_5$) are alkyl halides, such as methyl iodide, ethyl iodide, methyl bromide, ethyl bromide, methyl chloride, ethyl chloride, alkyl perfluoroalkylsulfonates, such as methyl trifluoromethylsulfonate and ethyl trifluoromethyl-sulfonate, alkyl alkylsulfonates, such as methyl methylsulfonate and ethyl methylsulfonate, alkyl arylsulfonates, such as methyl p-tolylsulfonate and ethyl p-tolylsulfonate, oxonium salts, such as trimethyloxonium tetrafluoroborate and triethyloxonium tetrafluoroborate.

Particular preference is given to methyl iodide, ethyl iodide, methyl bromide, ethyl bromide, methyl chloride and ethyl chloride.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, sodium carbonate, potassium carbonate and calcium carbonate, and also alkali metal bicarbonates, such as sodium bicarbonate, or organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide and potassium tert-butoxide.

Particular preference is given to sodium carbonate, potassium carbonate, sodium hydride, potassium hydride, butyllithium and potassium tert-butoxide.

The bases are generally employed in equimolar amounts, based on the compound I. However, they can also be used in an excess of from 5 mol % to 30 mol %, preferably from 5 mol % to 10 mol %.

The starting materials are generally reacted with one another in approximately equimolar amounts. In terms of yield, but it may be advantageous to employ the alkylating agent in an excess of from 1 mol % to 20 mol %, preferably from 1 mol % to 10 mol %.

With a view to the biological activity of the compounds I, preference is given to the following meanings of the variables, in each case either on their own or in combination:

n is zero;
m is 3;
$X^1$ is chlorine;
$X^2$ is fluorine or chlorine, preferably fluorine;
Y is $C_1$-$C_4$-alkyl, $C_1$-$C_4$-haloalkyl or methoxy, in particular methyl, difluoromethyl, trifluoromethyl or methoxy; particularly preferably methyl or trifluoromethyl;
p is zero;
$R^1$ is fluorine, chlorine, $C_1$-$C_4$-alkyl or $C_1$-$C_4$-haloalkyl, in particular F, Cl, methyl, fluoromethyl, difluoromethyl, chlorofluoromethyl, chlorodifluoromethyl, dichlorofluoromethyl or trifluoromethyl;
  particularly preferably methyl, fluoromethyl, difluoromethyl, chlorofluoromethyl or trifluoromethyl, in particular difluoromethyl or trifluoromethyl;
  very particularly preferably difluoromethyl;
$R^2$ is hydrogen, fluorine or chlorine, in particular hydrogen or chlorine, particularly preferably hydrogen;
$R^3$ is hydrogen or methyl, in particular hydrogen;
W is oxygen.

In the case of m=3, the radicals $X^2$ are preferably located in the 2,4,5- or 3,4,5-position, in particular in the 3,4,5-position.

Particular preference is given to compounds I having the following substituent combinations in which the substituents are as defined below:
$X^2$ is fluorine or chlorine;
Y is methyl, difluoromethyl, trifluoromethyl or methoxy;
$R^1$ is F, chlorine, methyl, fluoromethyl, difluoromethyl, chlorofluoromethyl, chlorodifluoromethyl, dichlorofluoromethyl, trifluoromethyl;
$R^2$ is hydrogen, fluorine or chlorine;
$R^3$ is hydrogen or methyl;
W is oxygen.

Preference is furthermore also given to the following combinations of substituents having the following meanings:

$X^2$ is fluorine or chlorine;
n is zero;
p is zero;
$R^1$ is F, chlorine, methyl, fluoromethyl, difluoromethyl, chlorofluoromethyl, chlorodifluoromethyl, dichlorofluoromethyl or trifluoromethyl, in particular fluorine, chlorine, fluoromethyl, difluoromethyl, chlorofluoromethyl, chlorodifluoromethyl, dichlorofluoromethyl or trifluoromethyl;
$R^2$ is hydrogen, fluorine or chlorine;
$R^3$ is hydrogen;
W is oxygen.

Preference is also given to compounds I where m=2, in particular to those in which $R^1$ is methyl, fluoromethyl, chlorofluoromethyl or chlorodifluoromethyl and/or $R^2$ is hydrogen or chlorine, in particular hydrogen. Here, the radicals X are preferably located in the 2,4- or 3,4-position, in particular in the 3,4-position.

In particular with a view to their use as fungicides, preference is given to the compounds of the general formulae I-A and I-B:

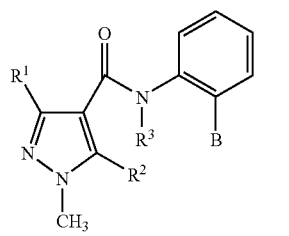
(I-A)

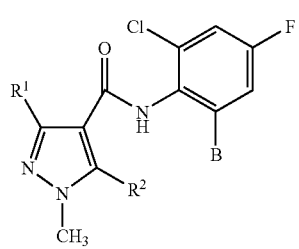
(I-B)

TABLE A

| No. | B | $R^1$ |
|---|---|---|
| 1 | 2,3-dichlorophenyl | $CF_3$ |
| 2 | 2,4-dichlorophenyl | $CF_3$ |
| 3 | 2,5-dichlorophenyl | $CF_3$ |
| 4 | 2,6-dichlorophenyl | $CF_3$ |
| 5 | 3,4-dichlorophenyl | $CF_3$ |
| 6 | 3,5-dichlorophenyl | $CF_3$ |
| 7 | 2,3-difluorophenyl | $CF_3$ |
| 8 | 2,4-difluorophenyl | $CF_3$ |
| 9 | 2,5-difluorophenyl | $CF_3$ |
| 10 | 2,6-difluorophenyl | $CF_3$ |
| 11 | 3,4-difluorophenyl | $CF_3$ |
| 12 | 3,5-difluorophenyl | $CF_3$ |
| 13 | 2-chloro-3-fluorophenyl | $CF_3$ |
| 14 | 2-chloro-4-fluorophenyl | $CF_3$ |
| 15 | 2-chloro-5-fluorophenyl | $CF_3$ |
| 16 | 2-chloro-6-fluorophenyl | $CF_3$ |
| 17 | 3-chloro-2-fluorophenyl | $CF_3$ |
| 18 | 3-chloro-4-fluorophenyl | $CF_3$ |
| 19 | 3-chloro-5-fluorophenyl | $CF_3$ |
| 20 | 3-chloro-6-fluorophenyl | $CF_3$ |

TABLE A-continued

| No. | B | $R^1$ |
|---|---|---|
| 21 | 4-chloro-2-fluorophenyl | $CF_3$ |
| 22 | 4-chloro-3-fluorophenyl | $CF_3$ |
| 23 | 2,3,4-trichlorophenyl | $CF_3$ |
| 24 | 2,3,5-trichlorophenyl | $CF_3$ |
| 25 | 2,3,6-trichlorophenyl | $CF_3$ |
| 26 | 2,4,5-trichlorophenyl | $CF_3$ |
| 27 | 2,4,6-trichlorophenyl | $CF_3$ |
| 28 | 3,4,5-trichlorophenyl | $CF_3$ |
| 29 | 2,3,4-trifluorophenyl | $CF_3$ |
| 30 | 2,3,5-trifluorophenyl | $CF_3$ |
| 31 | 2,3,6-trifluorophenyl | $CF_3$ |
| 32 | 2,4,5-trifluorophenyl | $CF_3$ |
| 33 | 2,4,6-trifluorophenyl | $CF_3$ |
| 34 | 3,4,5-trifluorophenyl | $CF_3$ |
| 35 | 2-chloro-3,4-difluorophenyl | $CF_3$ |
| 36 | 2-chloro-4,5-difluorophenyl | $CF_3$ |
| 37 | 2-chloro-5,6-difluorophenyl | $CF_3$ |
| 38 | 2-chloro-3,5-difluorophenyl | $CF_3$ |
| 39 | 2-chloro-3,6-difluorophenyl | $CF_3$ |
| 40 | 2-chloro-4,6-difluorophenyl | $CF_3$ |
| 41 | 3-chloro-2,4-difluorophenyl | $CF_3$ |
| 42 | 3-chloro-2,5-difluorophenyl | $CF_3$ |
| 43 | 3-chloro-2,6-difluorophenyl | $CF_3$ |
| 44 | 3-chloro-4,5-difluorophenyl | $CF_3$ |
| 45 | 3-chloro-4,6-difluorophenyl | $CF_3$ |
| 46 | 3-chloro-5,6-difluorophenyl | $CF_3$ |
| 47 | 4-chloro-2,3-difluorophenyl | $CF_3$ |
| 48 | 4-chloro-2,5-difluorophenyl | $CF_3$ |
| 49 | 4-chloro-2,6-difluorophenyl | $CF_3$ |
| 50 | 4-chloro-3,5-difluorophenyl | $CF_3$ |
| 51 | 2-fluoro-3,4-dichlorophenyl | $CF_3$ |
| 52 | 2-fluoro-4,5-dichlorophenyl | $CF_3$ |
| 53 | 2-fluoro-5,6-dichlorophenyl | $CF_3$ |
| 54 | 2-fluoro-3,5-dichlorophenyl | $CF_3$ |
| 55 | 2-fluoro-3,6-dichlorophenyl | $CF_3$ |
| 56 | 2-fluoro-4,6-dichlorophenyl | $CF_3$ |
| 57 | 3-fluoro-2,4-dichlorophenyl | $CF_3$ |
| 58 | 3-fluoro-2,5-dichlorophenyl | $CF_3$ |
| 59 | 3-fluoro-2,6-dichlorophenyl | $CF_3$ |
| 60 | 3-fluoro-4,5-dichlorophenyl | $CF_3$ |
| 61 | 3-fluoro-4,6-dichlorophenyl | $CF_3$ |
| 62 | 3-fluoro-5,6-dichlorophenyl | $CF_3$ |
| 63 | 4-fluoro-2,3-dichlorophenyl | $CF_3$ |
| 64 | 4-fluoro-2,5-dichlorophenyl | $CF_3$ |
| 65 | 4-fluoro-2,6-dichlorophenyl | $CF_3$ |
| 66 | 4-fluoro-3,5-dichlorophenyl | $CF_3$ |
| 67 | 2,3-dichlorophenyl | $CHF_2$ |
| 68 | 2,4-dichlorophenyl | $CHF_2$ |
| 69 | 2,5-dichlorophenyl | $CHF_2$ |
| 70 | 2,6-dichlorophenyl | $CHF_2$ |
| 71 | 3,4-dichlorophenyl | $CHF_2$ |
| 72 | 3,5-dichlorophenyl | $CHF_2$ |
| 73 | 2,3-difluorophenyl | $CHF_2$ |
| 74 | 2,4-difluorophenyl | $CHF_2$ |
| 75 | 2,5-difluorophenyl | $CHF_2$ |
| 76 | 2,6-difluorophenyl | $CHF_2$ |
| 77 | 3,4-difluorophenyl | $CHF_2$ |
| 78 | 3,5-difluorophenyl | $CHF_2$ |
| 79 | 2-chloro-3-fluorophenyl | $CHF_2$ |
| 80 | 2-chloro-4-fluorophenyl | $CHF_2$ |
| 81 | 2-chloro-5-fluorophenyl | $CHF_2$ |
| 82 | 2-chloro-6-fluorophenyl | $CHF_2$ |
| 83 | 3-chloro-2-fluorophenyl | $CHF_2$ |
| 84 | 3-chloro-4-fluorophenyl | $CHF_2$ |
| 85 | 3-chloro-5-fluorophenyl | $CHF_2$ |
| 86 | 3-chloro-6-fluorophenyl | $CHF_2$ |
| 87 | 4-chloro-2-fluorophenyl | $CHF_2$ |
| 88 | 4-chloro-3-fluorophenyl | $CHF_2$ |
| 89 | 2,3,4-trichlorophenyl | $CHF_2$ |
| 90 | 2,3,5-trichlorophenyl | $CHF_2$ |
| 91 | 2,3,6-trichlorophenyl | $CHF_2$ |
| 92 | 2,4,5-trichlorophenyl | $CHF_2$ |
| 93 | 2,4,6-trichlorophenyl | $CHF_2$ |
| 94 | 3,4,5-trichlorophenyl | $CHF_2$ |
| 95 | 2,3,4-trifluorophenyl | $CHF_2$ |
| 96 | 2,3,5-trifluorophenyl | $CHF_2$ |
| 97 | 2,3,6-trifluorophenyl | $CHF_2$ |
| 98 | 2,4,5-trifluorophenyl | $CHF_2$ |

TABLE A-continued

| No. | B | R¹ |
|---|---|---|
| 99 | 2,4,6-trifluorophenyl | CHF$_2$ |
| 100 | 3,4,5-trifluorophenyl | CHF$_2$ |
| 101 | 2-chloro-3,4-difluorophenyl | CHF$_2$ |
| 102 | 2-chloro-4,5-difluorophenyl | CHF$_2$ |
| 103 | 2-chloro-5,6-difluorophenyl | CHF$_2$ |
| 104 | 2-chloro-3,5-difluorophenyl | CHF$_2$ |
| 105 | 2-chloro-3,6-difluorophenyl | CHF$_2$ |
| 106 | 2-chloro-4,6-difluorophenyl | CHF$_2$ |
| 107 | 3-chloro-2,4-difluorophenyl | CHF$_2$ |
| 108 | 3-chloro-2,5-difluorophenyl | CHF$_2$ |
| 109 | 3-chloro-2,6-difluorophenyl | CHF$_2$ |
| 110 | 3-chloro-4,5-difluorophenyl | CHF$_2$ |
| 111 | 3-chloro-4,6-difluorophenyl | CHF$_2$ |
| 112 | 3-chloro-5,6-difluorophenyl | CHF$_2$ |
| 113 | 4-chloro-2,3-difluorophenyl | CHF$_2$ |
| 114 | 4-chloro-2,5-difluorophenyl | CHF$_2$ |
| 115 | 4-chloro-2,6-difluorophenyl | CHF$_2$ |
| 116 | 4-chloro-3,5-difluorophenyl | CHF$_2$ |
| 117 | 2-fluoro-3,4-dichlorophenyl | CHF$_2$ |
| 118 | 2-fluoro-4,5-dichlorophenyl | CHF$_2$ |
| 119 | 2-fluoro-5,6-dichlorophenyl | CHF$_2$ |
| 120 | 2-fluoro-3,5-dichlorophenyl | CHF$_2$ |
| 121 | 2-fluoro-3,6-dichlorophenyl | CHF$_2$ |
| 122 | 2-fluoro-4,6-dichlorophenyl | CHF$_2$ |
| 123 | 3-fluoro-2,4-dichlorophenyl | CHF$_2$ |
| 124 | 3-fluoro-2,5-dichlorophenyl | CHF$_2$ |
| 125 | 3-fluoro-2,6-dichlorophenyl | CHF$_2$ |
| 126 | 3-fluoro-4,5-dichlorophenyl | CHF$_2$ |
| 127 | 3-fluoro-4,6-dichlorophenyl | CHF$_2$ |
| 128 | 3-fluoro-5,6-dichlorophenyl | CHF$_2$ |
| 129 | 4-fluoro-2,3-dichlorophenyl | CHF$_2$ |
| 130 | 4-fluoro-2,5-dichlorophenyl | CHF$_2$ |
| 131 | 4-fluoro-2,6-dichlorophenyl | CHF$_2$ |
| 132 | 4-fluoro-3,5-dichlorophenyl | CHF$_2$ |
| 133 | 2,3-dichlorophenyl | CH$_2$F |
| 134 | 2,4-dichlorophenyl | CH$_2$F |
| 135 | 2,5-dichlorophenyl | CH$_2$F |
| 136 | 2,6-dichlorophenyl | CH$_2$F |
| 137 | 3,4-dichlorophenyl | CH$_2$F |
| 138 | 3,5-dichlorophenyl | CH$_2$F |
| 139 | 2,3-difluorophenyl | CH$_2$F |
| 140 | 2,4-difluorophenyl | CH$_2$F |
| 141 | 2,5-difluorophenyl | CH$_2$F |
| 142 | 2,6-difluorophenyl | CH$_2$F |
| 143 | 3,4-difluorophenyl | CH$_2$F |
| 144 | 3,5-difluorophenyl | CH$_2$F |
| 145 | 2-chloro-3-fluorophenyl | CH$_2$F |
| 146 | 2-chloro-4-fluorophenyl | CH$_2$F |
| 147 | 2-chloro-5-fluorophenyl | CH$_2$F |
| 148 | 2-chloro-6-fluorophenyl | CH$_2$F |
| 149 | 3-chloro-2-fluorophenyl | CH$_2$F |
| 150 | 3-chloro-4-fluorophenyl | CH$_2$F |
| 151 | 3-chloro-5-fluorophenyl | CH$_2$F |
| 152 | 3-chloro-6-fluorophenyl | CH$_2$F |
| 153 | 4-chloro-2-fluorophenyl | CH$_2$F |
| 154 | 4-chloro-3-fluorophenyl | CH$_2$F |
| 155 | 2,3,4-trichlorophenyl | CH$_2$F |
| 156 | 2,3,5-trichlorophenyl | CH$_2$F |
| 157 | 2,3,6-trichlorophenyl | CH$_2$F |
| 158 | 2,4,5-trichlorophenyl | CH$_2$F |
| 159 | 2,4,6-trichlorophenyl | CH$_2$F |
| 160 | 3,4,5-trichlorophenyl | CH$_2$F |
| 161 | 2,3,4-trifluorophenyl | CH$_2$F |
| 162 | 2,3,5-trifluorophenyl | CH$_2$F |
| 163 | 2,3,6-trifluorophenyl | CH$_2$F |
| 164 | 2,4,5-trifluorophenyl | CH$_2$F |
| 165 | 2,4,6-trifluorophenyl | CH$_2$F |
| 166 | 3,4,5-trifluorophenyl | CH$_2$F |
| 167 | 2-chloro-3,4-difluorophenyl | CH$_2$F |
| 168 | 2-chloro-4,5-difluorophenyl | CH$_2$F |
| 169 | 2-chloro-5,6-difluorophenyl | CH$_2$F |
| 170 | 2-chloro-3,5-difluorophenyl | CH$_2$F |
| 171 | 2-chloro-3,6-difluorophenyl | CH$_2$F |
| 172 | 2-chloro-4,6-difluorophenyl | CH$_2$F |
| 173 | 3-chloro-2,4-difluorophenyl | CH$_2$F |
| 174 | 3-chloro-2,5-difluorophenyl | CH$_2$F |
| 175 | 3-chloro-2,6-difluorophenyl | CH$_2$F |
| 176 | 3-chloro-4,5-difluorophenyl | CH$_2$F |
| 177 | 3-chloro-4,6-difluorophenyl | CH$_2$F |
| 178 | 3-chloro-5,6-difluorophenyl | CH$_2$F |
| 179 | 4-chloro-2,3-difluorophenyl | CH$_2$F |
| 180 | 4-chloro-2,5-difluorophenyl | CH$_2$F |
| 181 | 4-chloro-2,6-difluorophenyl | CH$_2$F |
| 182 | 4-chloro-3,5-difluorophenyl | CH$_2$F |
| 183 | 2-fluoro-3,4-dichlorophenyl | CH$_2$F |
| 184 | 2-fluoro-4,5-dichlorophenyl | CH$_2$F |
| 185 | 2-fluoro-5,6-dichlorophenyl | CH$_2$F |
| 186 | 2-fluoro-3,5-dichlorophenyl | CH$_2$F |
| 187 | 2-fluoro-3,6-dichlorophenyl | CH$_2$F |
| 188 | 2-fluoro-4,6-dichlorophenyl | CH$_2$F |
| 189 | 3-fluoro-2,4-dichlorophenyl | CH$_2$F |
| 190 | 3-fluoro-2,5-dichlorophenyl | CH$_2$F |
| 191 | 3-fluoro-2,6-dichlorophenyl | CH$_2$F |
| 192 | 3-fluoro-4,5-dichlorophenyl | CH$_2$F |
| 193 | 3-fluoro-4,6-dichlorophenyl | CH$_2$F |
| 194 | 3-fluoro-5,6-dichlorophenyl | CH$_2$F |
| 195 | 4-fluoro-2,3-dichlorophenyl | CH$_2$F |
| 196 | 4-fluoro-2,5-dichlorophenyl | CH$_2$F |
| 197 | 4-fluoro-2,6-dichlorophenyl | CH$_2$F |
| 198 | 4-fluoro-3,5-dichlorophenyl | CH$_2$F |
| 199 | 2,3-dichlorophenyl | CHFCl |
| 200 | 2,4-dichlorophenyl | CHFCl |
| 201 | 2,5-dichlorophenyl | CHFCl |
| 202 | 2,6-dichlorophenyl | CHFCl |
| 203 | 3,4-dichlorophenyl | CHFCl |
| 204 | 3,5-dichlorophenyl | CHFCl |
| 205 | 2,3-difluorophenyl | CHFCl |
| 206 | 2,4-difluorophenyl | CHFCl |
| 207 | 2,5-difluorophenyl | CHFCl |
| 208 | 2,6-difluorophenyl | CHFCl |
| 209 | 3,4-difluorophenyl | CHFCl |
| 210 | 3,5-difluorophenyl | CHFCl |
| 211 | 2-chloro-3-fluorophenyl | CHFCl |
| 212 | 2-chloro-4-fluorophenyl | CHFCl |
| 213 | 2-chloro-5-fluorophenyl | CHFCl |
| 214 | 2-chloro-6-fluorophenyl | CHFCl |
| 215 | 3-chloro-2-fluorophenyl | CHFCl |
| 216 | 3-chloro-4-fluorophenyl | CHFCl |
| 217 | 3-chloro-5-fluorophenyl | CHFCl |
| 218 | 3-chloro-6-fluorophenyl | CHFCl |
| 219 | 4-chloro-2-fluorophenyl | CHFCl |
| 220 | 4-chloro-3-fluorophenyl | CHFCl |
| 221 | 2,3,4-trichlorophenyl | CHFCl |
| 222 | 2,3,5-trichlorophenyl | CHFCl |
| 223 | 2,3,6-trichlorophenyl | CHFCl |
| 224 | 2,4,5-trichlorophenyl | CHFCl |
| 225 | 2,4,6-trichlorophenyl | CHFCl |
| 226 | 3,4,5-trichlorophenyl | CHFCl |
| 227 | 2,3,4-trifluorophenyl | CHFCl |
| 228 | 2,3,5-trifluorophenyl | CHFCl |
| 229 | 2,3,6-trifluorophenyl | CHFCl |
| 230 | 2,4,5-trifluorophenyl | CHFCl |
| 231 | 2,4,6-trifluorophenyl | CHFCl |
| 232 | 3,4,5-trifluorophenyl | CHFCl |
| 233 | 2-chloro-3,4-difluorophenyl | CHFCl |
| 234 | 2-chloro-4,5-difluorophenyl | CHFCl |
| 235 | 2-chloro-5,6-difluorophenyl | CHFCl |
| 236 | 2-chloro-3,5-difluorophenyl | CHFCl |
| 237 | 2-chloro-3,6-difluorophenyl | CHFCl |
| 238 | 2-chloro-4,6-difluorophenyl | CHFCl |
| 239 | 3-chloro-2,4-difluorophenyl | CHFCl |
| 240 | 3-chloro-2,5-difluorophenyl | CHFCl |
| 241 | 3-chloro-2,6-difluorophenyl | CHFCl |
| 242 | 3-chloro-4,5-difluorophenyl | CHFCl |
| 243 | 3-chloro-4,6-difluorophenyl | CHFCl |
| 244 | 3-chloro-5,6-difluorophenyl | CHFCl |
| 245 | 4-chloro-2,3-difluorophenyl | CHFCl |
| 246 | 4-chloro-2,5-difluorophenyl | CHFCl |
| 247 | 4-chloro-2,6-difluorophenyl | CHFCl |
| 248 | 4-chloro-3,5-difluorophenyl | CHFCl |
| 249 | 2-fluoro-3,4-dichlorophenyl | CHFCl |
| 250 | 2-fluoro-4,5-dichlorophenyl | CHFCl |
| 251 | 2-fluoro-5,6-dichlorophenyl | CHFCl |
| 252 | 2-fluoro-3,5-dichlorophenyl | CHFCl |
| 253 | 2-fluoro-3,6-dichlorophenyl | CHFCl |
| 254 | 2-fluoro-4,6-dichlorophenyl | CHFCl |

TABLE A-continued

| No. | B | R¹ |
|---|---|---|
| 255 | 3-fluoro-2,4-dichlorophenyl | CHFCl |
| 256 | 3-fluoro-2,5-dichlorophenyl | CHFCl |
| 257 | 3-fluoro-2,6-dichlorophenyl | CHFCl |
| 258 | 3-fluoro-4,5-dichlorophenyl | CHFCl |
| 259 | 3-fluoro-4,6-dichlorophenyl | CHFCl |
| 260 | 3-fluoro-5,6-dichlorophenyl | CHFCl |
| 261 | 4-fluoro-2,3-dichlorophenyl | CHFCl |
| 262 | 4-fluoro-2,5-dichlorophenyl | CHFCl |
| 263 | 4-fluoro-2,6-dichlorophenyl | CHFCl |
| 264 | 4-fluoro-3,5-dichlorophenyl | CHFCl |
| 265 | 2,3-dichlorophenyl | $CF_2Cl$ |
| 266 | 2,4-dichlorophenyl | $CF_2Cl$ |
| 267 | 2,5-dichlorophenyl | $CF_2Cl$ |
| 268 | 2,6-dichlorophenyl | $CF_2Cl$ |
| 269 | 3,4-dichlorophenyl | $CF_2Cl$ |
| 270 | 3,5-dichlorophenyl | $CF_2Cl$ |
| 271 | 2,3-difluorophenyl | $CF_2Cl$ |
| 272 | 2,4-difluorophenyl | $CF_2Cl$ |
| 273 | 2,5-difluorophenyl | $CF_2Cl$ |
| 274 | 2,6-difluorophenyl | $CF_2Cl$ |
| 275 | 3,4-difluorophenyl | $CF_2Cl$ |
| 276 | 3,5-difluorophenyl | $CF_2Cl$ |
| 277 | 2-chloro-3-fluorophenyl | $CF_2Cl$ |
| 278 | 2-chloro-4-fluorophenyl | $CF_2Cl$ |
| 279 | 2-chloro-5-fluorophenyl | $CF_2Cl$ |
| 280 | 2-chloro-6-fluorophenyl | $CF_2Cl$ |
| 281 | 3-chloro-2-fluorophenyl | $CF_2Cl$ |
| 282 | 3-chloro-4-fluorophenyl | $CF_2Cl$ |
| 283 | 3-chloro-5-fluorophenyl | $CF_2Cl$ |
| 284 | 3-chloro-6-fluorophenyl | $CF_2Cl$ |
| 285 | 4-chloro-2-fluorophenyl | $CF_2Cl$ |
| 286 | 4-chloro-3-fluorophenyl | $CF_2Cl$ |
| 287 | 2,3,4-trichlorophenyl | $CF_2Cl$ |
| 288 | 2,3,5-trichlorophenyl | $CF_2Cl$ |
| 289 | 2,3,6-trichlorophenyl | $CF_2Cl$ |
| 290 | 2,4,5-trichlorophenyl | $CF_2Cl$ |
| 291 | 2,4,6-trichlorophenyl | $CF_2Cl$ |
| 292 | 3,4,5-trichlorophenyl | $CF_2Cl$ |
| 293 | 2,3,4-trifluorophenyl | $CF_2Cl$ |
| 294 | 2,3,5-trifluorophenyl | $CF_2Cl$ |
| 295 | 2,3,6-trifluorophenyl | $CF_2Cl$ |
| 296 | 2,4,5-trifluorophenyl | $CF_2Cl$ |
| 297 | 2,4,6-trifluorophenyl | $CF_2Cl$ |
| 298 | 3,4,5-trifluorophenyl | $CF_2Cl$ |
| 299 | 2-chloro-3,4-difluorophenyl | $CF_2Cl$ |
| 300 | 2-chloro-4,5-difluorophenyl | $CF_2Cl$ |
| 301 | 2-chloro-5,6-difluorophenyl | $CF_2Cl$ |
| 302 | 2-chloro-3,5-difluorophenyl | $CF_2Cl$ |
| 303 | 2-chloro-3,6-difluorophenyl | $CF_2Cl$ |
| 304 | 2-chloro-4,6-difluorophenyl | $CF_2Cl$ |
| 305 | 3-chloro-2,4-difluorophenyl | $CF_2Cl$ |
| 306 | 3-chloro-2,5-difluorophenyl | $CF_2Cl$ |
| 307 | 3-chloro-2,6-difluorophenyl | $CF_2Cl$ |
| 308 | 3-chloro-4,5-difluorophenyl | $CF_2Cl$ |
| 309 | 3-chloro-4,6-difluorophenyl | $CF_2Cl$ |
| 310 | 3-chloro-5,6-difluorophenyl | $CF_2Cl$ |
| 311 | 4-chloro-2,3-difluorophenyl | $CF_2Cl$ |
| 312 | 4-chloro-2,5-difluorophenyl | $CF_2Cl$ |
| 313 | 4-chloro-2,6-difluorophenyl | $CF_2Cl$ |
| 314 | 4-chloro-3,5-difluorophenyl | $CF_2Cl$ |
| 315 | 2-fluoro-3,4-dichlorophenyl | $CF_2Cl$ |
| 316 | 2-fluoro-4,5-dichlorophenyl | $CF_2Cl$ |
| 317 | 2-fluoro-5,6-dichlorophenyl | $CF_2Cl$ |
| 318 | 2-fluoro-3,5-dichlorophenyl | $CF_2Cl$ |
| 319 | 2-fluoro-3,6-dichlorophenyl | $CF_2Cl$ |
| 320 | 2-fluoro-4,6-dichlorophenyl | $CF_2Cl$ |
| 321 | 3-fluoro-2,4-dichlorophenyl | $CF_2Cl$ |
| 322 | 3-fluoro-2,5-dichlorophenyl | $CF_2Cl$ |
| 323 | 3-fluoro-2,6-dichlorophenyl | $CF_2Cl$ |
| 324 | 3-fluoro-4,5-dichlorophenyl | $CF_2Cl$ |
| 325 | 3-fluoro-4,6-dichlorophenyl | $CF_2Cl$ |
| 326 | 3-fluoro-5,6-dichlorophenyl | $CF_2Cl$ |
| 327 | 4-fluoro-2,3-dichlorophenyl | $CF_2Cl$ |
| 328 | 4-fluoro-2,5-dichlorophenyl | $CF_2Cl$ |
| 329 | 4-fluoro-2,6-dichlorophenyl | $CF_2Cl$ |
| 330 | 4-fluoro-3,5-dichlorophenyl | $CF_2Cl$ |
| 331 | 2,3-dichlorophenyl | $CFCl_2$ |
| 332 | 2,4-dichlorophenyl | $CFCl_2$ |
| 333 | 2,5-dichlorophenyl | $CFCl_2$ |
| 334 | 2,6-dichlorophenyl | $CFCl_2$ |
| 335 | 3,4-dichlorophenyl | $CFCl_2$ |
| 336 | 3,5-dichlorophenyl | $CFCl_2$ |
| 337 | 2,3-difluorophenyl | $CFCl_2$ |
| 338 | 2,4-difluorophenyl | $CFCl_2$ |
| 339 | 2,5-difluorophenyl | $CFCl_2$ |
| 340 | 2,6-difluorophenyl | $CFCl_2$ |
| 341 | 3,4-difluorophenyl | $CFCl_2$ |
| 342 | 3,5-difluorophenyl | $CFCl_2$ |
| 343 | 2-chloro-3-fluorophenyl | $CFCl_2$ |
| 344 | 2-chloro-4-fluorophenyl | $CFCl_2$ |
| 345 | 2-chloro-5-fluorophenyl | $CFCl_2$ |
| 346 | 2-chloro-6-fluorophenyl | $CFCl_2$ |
| 347 | 3-chloro-2-fluorophenyl | $CFCl_2$ |
| 348 | 3-chloro-4-fluorophenyl | $CFCl_2$ |
| 349 | 3-chloro-5-fluorophenyl | $CFCl_2$ |
| 350 | 3-chloro-6-fluorophenyl | $CFCl_2$ |
| 351 | 4-chloro-2-fluorophenyl | $CFCl_2$ |
| 352 | 4-chloro-3-fluorophenyl | $CFCl_2$ |
| 353 | 2,3,4-trichlorophenyl | $CFCl_2$ |
| 354 | 2,3,5-trichlorophenyl | $CFCl_2$ |
| 355 | 2,3,6-trichlorophenyl | $CFCl_2$ |
| 356 | 2,4,5-trichlorophenyl | $CFCl_2$ |
| 357 | 2,4,6-trichlorophenyl | $CFCl_2$ |
| 358 | 3,4,5-trichlorophenyl | $CFCl_2$ |
| 359 | 2,3,4-trifluorophenyl | $CFCl_2$ |
| 360 | 2,3,5-trifluorophenyl | $CFCl_2$ |
| 361 | 2,3,6-trifluorophenyl | $CFCl_2$ |
| 362 | 2,4,5-trifluorophenyl | $CFCl_2$ |
| 363 | 2,4,6-trifluorophenyl | $CFCl_2$ |
| 364 | 3,4,5-trifluorophenyl | $CFCl_2$ |
| 365 | 2-chloro-3,4-difluorophenyl | $CFCl_2$ |
| 366 | 2-chloro-4,5-difluorophenyl | $CFCl_2$ |
| 367 | 2-chloro-5,6-difluorophenyl | $CFCl_2$ |
| 368 | 2-chloro-3,5-difluorophenyl | $CFCl_2$ |
| 369 | 2-chloro-3,6-difluorophenyl | $CFCl_2$ |
| 370 | 2-chloro-4,6-difluorophenyl | $CFCl_2$ |
| 371 | 3-chloro-2,4-difluorophenyl | $CFCl_2$ |
| 372 | 3-chloro-2,5-difluorophenyl | $CFCl_2$ |
| 373 | 3-chloro-2,6-difluorophenyl | $CFCl_2$ |
| 374 | 3-chloro-4,5-difluorophenyl | $CFCl_2$ |
| 375 | 3-chloro-4,6-difluorophenyl | $CFCl_2$ |
| 376 | 3-chloro-5,6-difluorophenyl | $CFCl_2$ |
| 377 | 4-chloro-2,3-difluorophenyl | $CFCl_2$ |
| 378 | 4-chloro-2,5-difluorophenyl | $CFCl_2$ |
| 379 | 4-chloro-2,6-difluorophenyl | $CFCl_2$ |
| 380 | 4-chloro-3,5-difluorophenyl | $CFCl_2$ |
| 381 | 2-fluoro-3,4-dichlorophenyl | $CFCl_2$ |
| 382 | 2-fluoro-4,5-dichlorophenyl | $CFCl_2$ |
| 383 | 2-fluoro-5,6-dichlorophenyl | $CFCl_2$ |
| 384 | 2-fluoro-3,5-dichlorophenyl | $CFCl_2$ |
| 385 | 2-fluoro-3,6-dichlorophenyl | $CFCl_2$ |
| 386 | 2-fluoro-4,6-dichlorophenyl | $CFCl_2$ |
| 387 | 3-fluoro-2,4-dichlorophenyl | $CFCl_2$ |
| 388 | 3-fluoro-2,5-dichlorophenyl | $CFCl_2$ |
| 389 | 3-fluoro-2,6-dichlorophenyl | $CFCl_2$ |
| 390 | 3-fluoro-4,5-dichlorophenyl | $CFCl_2$ |
| 391 | 3-fluoro-4,6-dichlorophenyl | $CFCl_2$ |
| 392 | 3-fluoro-5,6-dichlorophenyl | $CFCl_2$ |
| 393 | 4-fluoro-2,3-dichlorophenyl | $CFCl_2$ |
| 394 | 4-fluoro-2,5-dichlorophenyl | $CFCl_2$ |
| 395 | 4-fluoro-2,6-dichlorophenyl | $CFCl_2$ |
| 396 | 4-fluoro-3,5-dichlorophenyl | $CFCl_2$ |
| 397 | 2,3-dichlorophenyl | $CH_3$ |
| 398 | 2,4-dichlorophenyl | $CH_3$ |
| 399 | 2,5-dichlorophenyl | $CH_3$ |
| 400 | 2,6-dichlorophenyl | $CH_3$ |
| 401 | 3,4-dichlorophenyl | $CH_3$ |
| 402 | 3,5-dichlorophenyl | $CH_3$ |
| 403 | 2,3-difluorophenyl | $CH_3$ |
| 404 | 2,4-difluorophenyl | $CH_3$ |
| 405 | 2,5-difluorophenyl | $CH_3$ |
| 406 | 2,6-difluorophenyl | $CH_3$ |
| 407 | 3,4-difluorophenyl | $CH_3$ |
| 408 | 3,5-difluorophenyl | $CH_3$ |
| 409 | 2-chloro-3-fluorophenyl | $CH_3$ |
| 410 | 2-chloro-4-fluorophenyl | $CH_3$ |

TABLE A-continued

| No. | B | R¹ |
|---|---|---|
| 411 | 2-chloro-5-fluorophenyl | $CH_3$ |
| 412 | 2-chloro-6-fluorophenyl | $CH_3$ |
| 413 | 3-chloro-2-fluorophenyl | $CH_3$ |
| 414 | 3-chloro-4-fluorophenyl | $CH_3$ |
| 415 | 3-chloro-5-fluorophenyl | $CH_3$ |
| 416 | 3-chloro-6-fluorophenyl | $CH_3$ |
| 417 | 4-chloro-2-fluorophenyl | $CH_3$ |
| 418 | 4-chloro-3-fluorophenyl | $CH_3$ |
| 419 | 2,3,4-trichlorophenyl | $CH_3$ |
| 420 | 2,3,5-trichlorophenyl | $CH_3$ |
| 421 | 2,3,6-trichlorophenyl | $CH_3$ |
| 422 | 2,4,5-trichlorophenyl | $CH_3$ |
| 423 | 2,4,6-trichlorophenyl | $CH_3$ |
| 424 | 3,4,5-trichlorophenyl | $CH_3$ |
| 425 | 2,3,4-trifluorophenyl | $CH_3$ |
| 426 | 2,3,5-trifluorophenyl | $CH_3$ |
| 427 | 2,3,6-trifluorophenyl | $CH_3$ |
| 428 | 2,4,5-trifluorophenyl | $CH_3$ |
| 429 | 2,4,6-trifluorophenyl | $CH_3$ |
| 430 | 3,4,5-trifluorophenyl | $CH_3$ |
| 431 | 2-chloro-3,4-difluorophenyl | $CH_3$ |
| 432 | 2-chloro-4,5-difluorophenyl | $CH_3$ |
| 433 | 2-chloro-5,6-difluorophenyl | $CH_3$ |
| 434 | 2-chloro-3,5-difluorophenyl | $CH_3$ |
| 435 | 2-chloro-3,6-difluorophenyl | $CH_3$ |
| 436 | 2-chloro-4,6-difluorophenyl | $CH_3$ |
| 437 | 3-chloro-2,4-difluorophenyl | $CH_3$ |
| 438 | 3-chloro-2,5-difluorophenyl | $CH_3$ |
| 439 | 3-chloro-2,6-difluorophenyl | $CH_3$ |
| 440 | 3-chloro-4,5-difluorophenyl | $CH_3$ |
| 441 | 3-chloro-4,6-difluorophenyl | $CH_3$ |
| 442 | 3-chloro-5,6-difluorophenyl | $CH_3$ |
| 443 | 4-chloro-2,3-difluorophenyl | $CH_3$ |
| 444 | 4-chloro-2,5-difluorophenyl | $CH_3$ |
| 445 | 4-chloro-2,6-difluorophenyl | $CH_3$ |
| 446 | 4-chloro-3,5-difluorophenyl | $CH_3$ |
| 447 | 2-fluoro-3,4-dichlorophenyl | $CH_3$ |
| 448 | 2-fluoro-4,5-dichlorophenyl | $CH_3$ |
| 449 | 2-fluoro-5,6-dichlorophenyl | $CH_3$ |
| 450 | 2-fluoro-3,5-dichlorophenyl | $CH_3$ |
| 451 | 2-fluoro-3,6-dichlorophenyl | $CH_3$ |
| 452 | 2-fluoro-4,6-dichlorophenyl | $CH_3$ |
| 453 | 3-fluoro-2,4-dichlorophenyl | $CH_3$ |
| 454 | 3-fluoro-2,5-dichlorophenyl | $CH_3$ |
| 455 | 3-fluoro-2,6-dichlorophenyl | $CH_3$ |
| 456 | 3-fluoro-4,5-dichlorophenyl | $CH_3$ |
| 457 | 3-fluoro-4,6-dichlorophenyl | $CH_3$ |
| 458 | 3-fluoro-5,6-dichlorophenyl | $CH_3$ |
| 459 | 4-fluoro-2,3-dichlorophenyl | $CH_3$ |
| 460 | 4-fluoro-2,5-dichlorophenyl | $CH_3$ |
| 461 | 4-fluoro-2,6-dichlorophenyl | $CH_3$ |
| 462 | 4-fluoro-3,5-dichlorophenyl | $CH_3$ |

TABLE 1

Compounds of the general formula I-A in which $R^2$, $R^3$ are hydrogen and $R^1$ and B for each individual compound correspond in each case to one row of Table A, except for rows 1-22 and 67-88.

TABLE 2

Compounds of the general formula I-A in which $R^2$ is Cl, $R^3$ is hydrogen and
$R^1$ and B for each individual compound correspond in each case to one row of Table A.

TABLE 3

Compounds of the general formula I-A in which $R^2$ is F, $R^3$ is hydrogen and $R^1$ and B for each individual compound correspond in each case to one row of Table A except for rows 397 to 462.

TABLE 4

Compounds of the general formula I-A in which $R^2$ is hydrogen, $R^3$ is methyl
and $R^1$ and B for each individual compound correspond in each case to one row of Table A.

TABLE 5

Compounds of the general formula I-A in which $R^2$ is hydrogen, $R^3$ is ethyl and $R^1$ and B for each individual compound correspond in each case to one row of Table A.

TABLE 6

Compounds of the general formula I-B in which $R^2$ is hydrogen and $R^1$ and B for each individual compound correspond in each case to one row of Table A.

Preference is furthermore also given to the compounds of the general formulae I-C and I-D.

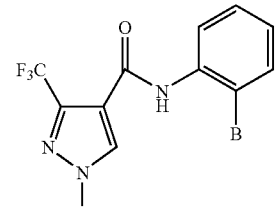

(I-C)

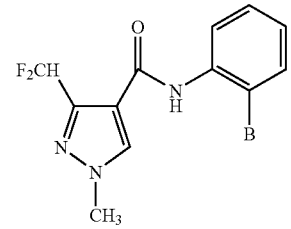

(I-D)

TABLE B

| No. | B |
|---|---|
| 1 | 2,3-dichloro-4-methylphenyl |
| 2 | 2,3-dichloro-4-methoxyphenyl |
| 3 | 2,3-dichloro-5-methylphenyl |
| 4 | 2,3-dichloro-5-methoxyphenyl |
| 5 | 2,3-dichloro-6-methylphenyl |
| 6 | 2,3-dichloro-6-methoxyphenyl |
| 7 | 2,3-difluoro-4-methylphenyl |
| 8 | 2,3-difluoro-4-methoxyphenyl |
| 9 | 2,3-difluoro-5-methylphenyl |
| 10 | 2,3-difluoro-5-methoxyphenyl |
| 11 | 2,3-difluoro-6-methylphenyl |
| 12 | 2,3-difluoro-6-methoxyphenyl |
| 13 | 2,4-dichloro-3-methylphenyl |
| 14 | 2,4-dichloro-3-methoxyphenyl |

TABLE B-continued

| No. | B |
|---|---|
| 15 | 2,4-dichloro-5-methylphenyl |
| 16 | 2,4-dichloro-5-methoxyphenyl |
| 17 | 2,4-dichloro-6-methylphenyl |
| 18 | 2,4-dichloro-6-methoxyphenyl |
| 19 | 2,4-difluoro-3-methylphenyl |
| 20 | 2,4-difluoro-3-methoxyphenyl |
| 21 | 2,4-difluoro-5-methylphenyl |
| 22 | 2,4-difluoro-5-methoxyphenyl |
| 23 | 2,4-difluoro-6-methylphenyl |
| 24 | 2,4-difluoro-6-methoxyphenyl |
| 25 | 2,5-dichloro-3-methylphenyl |
| 26 | 2,5-dichloro-3-methoxyphenyl |
| 27 | 2,5-dichloro-4-methylphenyl |
| 28 | 2,5-dichloro-4-methoxyphenyl |
| 29 | 2,5-dichloro-6-methylphenyl |
| 30 | 2,5-dichloro-6-methoxyphenyl |
| 31 | 2,5-difluoro-3-methylphenyl |
| 32 | 2,5-difluoro-3-methoxyphenyl |
| 33 | 2,5-difluoro-4-methylphenyl |
| 34 | 2,5-difluoro-4-methoxyphenyl |
| 35 | 2,5-difluoro-6-methylphenyl |
| 36 | 2,5-difluoro-6-methoxyphenyl |
| 37 | 2,6-dichloro-3-methylphenyl |
| 38 | 2,6-dichloro-3-methoxyphenyl |
| 39 | 2,6-dichloro-4-methylphenyl |
| 40 | 2,6-dichloro-4-methoxyphenyl |
| 41 | 2,6-difluoro-3-methylphenyl |
| 42 | 2,6-difluoro-3-methoxyphenyl |
| 43 | 2,6-difluoro-4-methylphenyl |
| 44 | 2,6-difluoro-4-methoxyphenyl |
| 45 | 3,4-dichloro-2-methylphenyl |
| 46 | 3,4-dichloro-2-methoxyphenyl |
| 47 | 3,4-dichloro-5-methylphenyl |
| 48 | 3,4-dichloro-5-methoxyphenyl |
| 49 | 3,4-dichloro-6-methylphenyl |
| 50 | 3,4-dichloro-6-methoxyphenyl |
| 51 | 3,4-difluoro-2-methylphenyl |
| 52 | 3,4-difluoro-2-methoxyphenyl |
| 53 | 3,4-difluoro-5-methylphenyl |
| 54 | 3,4-difluoro-5-methoxyphenyl |
| 55 | 3,4-difluoro-6-methylphenyl |
| 56 | 3,4-difluoro-6-methoxyphenyl |
| 57 | 3,5-dichloro-2-methylphenyl |
| 58 | 3,5-dichloro-2-methoxyphenyl |
| 59 | 3,5-dichloro-4-methylphenyl |
| 60 | 3,5-dichloro-4-methoxyphenyl |
| 61 | 3,5-difluoro-2-methylphenyl |
| 62 | 3,5-difluoro-2-methoxyphenyl |
| 63 | 3,5-difluoro-4-methylphenyl |
| 64 | 3,5-difluoro-4-methoxyphenyl |
| 65 | 2-chloro-3-fluoro-4-methylphenyl |
| 66 | 2-chloro-3-fluoro-4-methoxyphenyl |
| 67 | 2-chloro-3-fluoro-5-methylphenyl |
| 68 | 2-chloro-3-fluoro-5-methoxyphenyl |
| 69 | 2-chloro-3-fluoro-6-methylphenyl |
| 70 | 2-chloro-3-fluoro-6-methoxyphenyl |
| 71 | 2-chloro-4-fluoro-3-methylphenyl |
| 72 | 2-chloro-4-fluoro-3-methoxyphenyl |
| 73 | 2-chloro-4-fluoro-5-methylphenyl |
| 74 | 2-chloro-4-fluoro-5-methoxyphenyl |
| 75 | 2-chloro-4-fluoro-6-methylphenyl |
| 76 | 2-chloro-4-fluoro-6-methoxyphenyl |
| 77 | 2-chloro-5-fluoro-3-methylphenyl |
| 78 | 2-chloro-5-fluoro-3-methoxyphenyl |
| 79 | 2-chloro-5-fluoro-4-methylphenyl |
| 80 | 2-chloro-5-fluoro-4-methoxyphenyl |
| 81 | 2-chloro-5-fluoro-6-methylphenyl |
| 82 | 2-chloro-5-fluoro-6-methoxyphenyl |
| 83 | 2-chloro-6-fluoro-3-methylphenyl |
| 84 | 2-chloro-6-fluoro-3-methoxyphenyl |
| 85 | 2-chloro-6-fluoro-4-methylphenyl |
| 86 | 2-chloro-6-fluoro-4-methoxyphenyl |
| 87 | 2-chloro-6-fluoro-5-methylphenyl |
| 88 | 2-chloro-6-fluoro-5-methoxyphenyl |
| 89 | 2-fluoro-3-chloro-4-methylphenyl |
| 90 | 2-fluoro-3-chloro-4-methoxyphenyl |
| 91 | 2-fluoro-3-chloro-5-methylphenyl |
| 92 | 2-fluoro-3-chloro-5-methoxyphenyl |
| 93 | 2-fluoro-3-chloro-6-methylphenyl |
| 94 | 2-fluoro-3-chloro-6-methoxyphenyl |
| 95 | 2-fluoro-4-chloro-3-methylphenyl |
| 96 | 2-fluoro-4-chloro-3-methoxyphenyl |
| 97 | 2-fluoro-4-chloro-5-methylphenyl |
| 98 | 2-fluoro-4-chloro-5-methoxyphenyl |
| 99 | 2-fluoro-4-chloro-6-methylphenyl |
| 100 | 2-fluoro-4-chloro-6-methoxyphenyl |
| 101 | 2-fluoro-5-chloro-3-methylphenyl |
| 102 | 2-fluoro-5-chloro-3-methoxyphenyl |
| 103 | 2-fluoro-5-chloro-4-methylphenyl |
| 104 | 2-fluoro-5-chloro-4-methoxyphenyl |
| 105 | 2-fluoro-5-chloro-6-methylphenyl |
| 106 | 2-fluoro-5-chloro-6-methoxyphenyl |
| 107 | 3-chloro-4-fluoro-2-methylphenyl |
| 108 | 3-chloro-4-fluoro-2-methoxyphenyl |
| 109 | 3-chloro-4-fluoro-5-methylphenyl |
| 110 | 3-chloro-4-fluoro-5-methoxyphenyl |
| 111 | 3-chloro-4-fluoro-6-methylphenyl |
| 112 | 3-chloro-4-fluoro-6-methoxyphenyl |
| 113 | 3-fluoro-4-chloro-2-methylphenyl |
| 114 | 3-fluoro-4-chloro-2-methoxyphenyl |
| 115 | 3-fluoro-4-chloro-5-methylphenyl |
| 116 | 3-fluoro-4-chloro-5-methoxyphenyl |
| 117 | 3-fluoro-4-chloro-6-methylphenyl |
| 118 | 3-fluoro-4-chloro-6-methoxyphenyl |
| 119 | 3-chloro-5-fluoro-2-methylphenyl |
| 120 | 3-chloro-5-fluoro-2-methoxyphenyl |
| 121 | 3-chloro-5-fluoro-4-methylphenyl |
| 122 | 3-chloro-5-fluoro-4-methoxyphenyl |
| 123 | 3-chloro-5-fluoro-6-methylphenyl |
| 124 | 3-chloro-5-fluoro-6-methoxyphenyl |

TABLE 7

Compounds of the general formula I-C in which B for each individual compound correspond in each case to one row of Table B.

TABLE 8

Compounds of the general formula I-D in which B for each individual compound correspond in each case to one row of Table B.

The compounds I are suitable for use as fungicides. They are distinguished by excellent activity against a broad spectrum of phytopathogenic fungi in particular from the classes of the Ascomycetes, Deuteromycetes, Peronasporomycetes (syn. Oomycetes) and Basidiomycetes. Some of them are systemically active and can be used in crop protection as foliar fungicides, as soil fungicides and as fungicides for seed dressing.

They are particularly important in the control of a large number of fungi on various crop plants, such as wheat, rye, barley, oats, rice, corn, grass, bananas, cotton, soybeans, coffee, sugar cane, grapevines, fruit and ornamental plants and vegetables, such as cucumbers, beans, tomatoes, potatoes and cucurbits, and also the seeds of these plants.

They are especially suitable for controlling the following plant diseases:

*Alternaria* species on vegetables, rapeseed, sugar beet and fruit and rice (for example *A. solani* or *A. alternata* on potato and other plants),
*Aphanomyces* species on sugar beet and vegetables,
*Bipolaris* and *Drechslera* species on corn, cereals, rice and lawns (for example *D. teres* on barley, *D. tritci-repentis* on wheat),
*Blumeria graminis* (powdery mildew) on cereals, Botrytis cinerea (gray mold) on strawberries, vegetables, flowers and grapevines,
Bremia lactucae on lettuce,
Cercospora species on corn, soybeans, rice and sugar beet (for example C. beticula on sugar beet),
Cochliobolus species on corn, cereals, rice (for example Cochliobolus sativus on cereals, Cochliobolus miyabeanus on rice),
Colletotricum species on soybeans, cotton and other plants (for example C. acutatum on various plants),
Exserohilum speciea on corn,
Erysiphe cichoracearum and Sphaerotheca fuliginea on cucurbits,
Fusarium and Verticillium species (for example V. dahliae) on various plants (for example F. graminearum on wheat),
Gaeumanomyces graminis on cereals,
Gibberella species on cereals and rice (for example Gibberella fujikuroi on rice),
Grainstaining complex on rice,
Helminthosporium species (for example H. graminicola) on corn and rice,
Michrodochium nivale on cereals,
Mycosphaerella species on cereals, bananas and peanuts (M. graminicola on wheat, M. fijiesis on bananas),
Phakopsara pachyrhizi and Phakopsara meibomiae on soybeans,
Phomopsis species on soybeans, sunflowers and grapevines (P. viticola on grapevines, P. helianthii on sunflowers),
Phytophthora infestans on potatoes and tomatoes,
Plasmopara viticola on grapevines,
Podosphaera leucotricha on apples,
Pseudocercosporella herpotrichoides on cereals,
Pseudoperonospora species on hops and cucurbits (for example P. cubenis on cucumbers),
Puccinia species on cereals, corn and asparagus (P. triticina and P. striformis on wheat, P. asparagi on asparagus),
Pyrenophora species on cereals,
Pyricularia oryzae, Corticium sasakii, Sarocladium oryzae, S. attenuatum, Entyloma oryzae on rice,
Pyricularia grisea on lawns and cereals,
Pythium spp. on lawns, rice, corn, cotton, rapeseed, sunflowers, sugar beet, vegetables and other plants,
Rhizoctonia-species (for example R. solani) on cotton, rice, potatoes, lawns, corn, rapeseed, potatoes, sugar beet, vegetables and other plants,
Sclerotinia species (for example S. sclerotiorum) on rapeseed, sunflowers and other plants,
Septoria tritici and Stagonospora nodorum on wheat,
Erysiphe (syn. Uncinulanecator) on grapevines,
Setospaeria species on corn and lawns,
Sphacelotheca reilinia on corn,
Thievaliopsis species on soybeans and cotton,
Tilletia species on cereals,
Ustilago species on cereals, corn and sugar beet and
Venturia species (scab) on apples and pears (for example V. inaequalis on apples).

The compounds I are furthermore suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as Ophiostoma spp., Ceratocystis spp., Aureobasidium pullulans, Sclerophoma spp., Chaetomium spp., Humicola spp., Petriella spp., Trichurus spp.; Basidiomycetes, such as Coniophora spp., Coriolus spp., Gloeophyllum spp., Lentinus spp., Pleurotus spp., Poria spp., Serpula spp. and Tyromyces spp., Deuteromycetes, such as Aspergillus spp., Cladosporium spp., Penicillium spp., Trichoderma spp., Alternaria spp., Paecilomyces spp. and Zygomycetes, such as Mucor spp., additionally in the protection of materials the following yeasts: Candida spp. and Saccharomyces cerevisae.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, for example by dusting, coating or drenching seed, amounts of active compound of from 1 to 1000 g/100 kg, preferably from 5 to 100 g/100 kg, of seed are generally necessary.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

Formulations for the treatment of seed may additionally comprise binders and/or gelling agents and, if appropriate, colorants.

Binders may be added to increase the adhesion of the active compounds on the seed after the treatment. Suitable binders are, for example, EO/PO block copolymer surfactants, but also polyvinyl alcohols, polyvinylpyrrolidones, polyacrylates, polymethacrylates, polybutenes, polyisobutylenes, polystyrenes, polyethylenamines, polyethylenamides, polyethylenimines (Lupasol®, Polymin®), polyethers, polyurethanes, polyvinyl acetates, tylose and copolymers of these polymers. A suitable gelling agent is, for example, carrageen (Satiagel®).

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The concentrations of active compound in the ready-for-use preparations can be varied within relatively wide ranges. In general, they are between 0.0001 and 10%, preferably between 0.01 and 1%.

The active compounds can also be used with great success in the ultra-low volume (ULV) process, it being possible to apply formulations with more than 95% by weight of active compound or even to apply the active compound without additives.

For the treatment of seed, the formulations in question give, after two- to ten-fold dilution, active compound concentrations of from 0.01 to 60% by weight, preferably from 0.1 to 40% by weight, in the ready-to-use preparations.

The following are examples of formulations: 1. Products for dilution with water
A) Water-Soluble Concentrates (SL)

10 parts by weight of a compound I according to the invention are dissolved in 90 parts by weight of water or in a water-soluble solvent. As an alternative, wetting agents or other auxiliaries are added. The active compound dissolves upon dilution with water. In this way, a formulation having a content of 10% by weight of active compound is obtained.
B) Dispersible Concentrates (DC)

20 parts by weight of a compound I according to the invention are dissolved in 70 parts by weight of cyclohexanone with addition of 10 parts by weight of a dispersant, for example polyvinylpyrrolidone. Dilution with water gives a dispersion. The active compound content is 20% by weight.
C) Emulsifiable Concentrates (EC)

15 parts by weight of a compound I according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.
D) Emulsions (EW, EO)

25 parts by weight of a compound I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (for example Ultraturrax) and made into a homogeneous emulsion. Dilution with water gives an emulsion. The formulation has an active compound content of 25% by weight.
E) Suspensions (SC, OD)

In an agitated ball mill, 20 parts by weight of a compound I according to the invention are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.
F) Water-Dispersible Granules and Water-Soluble Granules (WG, SG)

50 parts by weight of a compound I according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.
G) Water-Dispersible Powders and Water-Soluble Powders (WP, SP)

75 parts by weight of a compound I according to the invention are ground in a rotor-stator mill with addition of 25 parts by weight of dispersants, wetting agents and silica gel. Dilution with water gives a stable dispersion or solution of the active compound. The active compound content of the formulation is 75% by weight.
2. Products to be Applied Undiluted
H) Dustable Powders (DP)

5 parts by weight of a compound I according to the invention are ground finely and mixed intimately with 95 parts by weight of finely divided kaolin. This gives a dustable product having an active compound content of 5% by weight.
J) Granules (GR, FG, GG, MG)

0.5 part by weight of a compound I according to the invention is ground finely and associated with 99.5 parts by weight of carriers. Current methods are extrusion, spray-drying or the fluidized bed. This gives granules to be applied undiluted having an active compound content of 0.5% by weight.
K) ULV Solutions (UL)

10 parts by weight of a compound I according to the invention are dissolved in 90 parts by weight of an organic solvent, for example xylene. This gives a product to be applied undiluted having an active compound content of 10% by weight.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (wettable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply formulations comprising over 95% by weight of active compound, or even to apply the active compound without additives. Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:100 to 100:1, preferably 1:10 to 10:1.

Suitable adjuvants in this sense are in particular: organically modified polysiloxanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

The compositions according to the invention can, in the use form as fungicides, also be present together with other active compounds, for example with herbicides, insecticides, growth regulators, such as prohexadione-Ca, fungicides or else with fertilizers. By mixing the compounds I or the compositions comprising them with one or more further active compounds, in particular fungicides, it is in many cases possible to broaden the activity spectrum or to prevent the development of resistance. In many cases, synergistic effects are obtained.

The following list of fungicides, with which the compounds according to the invention can be used in conjunction, is intended to illustrate the possible combinations but does not limit them:

Strobilurins
  azoxystrobin, dimoxystrobin, enestrostrobin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)-ethyl]benzyl)carbamate, methyl 2-(ortho-(2,5-dimethylphenyloxymethylene)phenyl)-3-methoxyacrylate.

Carboxamides
  carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;
  carboxylic acid morpholides: dimethomorph, flumorph;
  benzamides: flumetover, fluopicolide (picobenzamid), zoxamide;
  other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

Azoles
  triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;
  imidazoles: cyazofamid, imazalil, pefurazoate, prochloraz, triflumizole;
  benzimidazoles: benomyl, carbendazim, fuberidazole, thiabendazole;
  others: ethaboxam, etridiazole, hymexazole;

Nitrogenous Heterocyclyl Compounds
  pyridines: fluazinam, pyrifenox, 3-[5-(4-chlorophenyl)-2,3-dimethylisoxazolidin-3-yl]-pyridine;
  pyrimidines: bupirimate, cyprodinil, ferimzone, fenarimol, mepanipyrim, nuarimol, pyrimethanil;
  piperazines: triforine;
  pyrroles: fludioxonil, fenpiclonil;
  morpholines: aldimorph, dodemorph, fenpropimorph, tridemorph;
  dicarboximides: iprodione, procymidone, vinclozolin;
  others: acibenzolar-5-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

Carbamates and Dithiocarbamates
  dithiocarbamates: ferbam, mancozeb, maneb, metiram, metam, propineb, thiram, zineb, ziram;
  carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;

Other Fungicides
  guanidines: dodine, iminoctadine, guazatine;
  antibiotics: kasugamycin, polyoxins, streptomycin, validamycin A;
  organometallic compounds: fentin salts;

sulfur-containing heterocyclyl compounds: isoprothiolane, dithianon;
organophosphorus compounds: edifenphos, fosetyl, fosetyl-aluminum, iprobenfos, pyrazophos, tolclofos-methyl, phosphorous acid and its salts;
organochlorine compounds: thiophanate-methyl, chlorothalonil, dichlofluanid, tolylfluanid, flusulfamide, phthalide, hexachlorobenzene, pencycuron, quintozene;
nitrophenyl derivatives: binapacryl, dinocap, dinobuton;
inorganic active compounds: Bordeaux mixture, copper acetate, copper hydroxide, copper oxychloride, basic copper sulfate, sulfur;
others: spiroxamine, cyflufenamid, cymoxanil, metrafenone.

SYNTHESIS EXAMPLES

Example 1

N-(3'-chloro-4'-fluorobiphenyl-2-yl)-1,3-dimethyl-1H-pyrazole-4-carboxamide

At room temperature, 0.47 g of 3'-chloro-4'-fluoro-2-aminobiphenyl and 0.82 g of bis(2-oxo-3-oxazolidinyl)phosphoryl chloride were added to a solution of 0.30 g of 1,3-dimethyl-1H-pyrazole-4-carboxylic acid and 0.43 g of triethylamine in 30 ml of dichloromethane. The mixture was stirred at room temperature for 12 hours. The mixture was then washed successively twice with dilute hydrochloric acid, twice with aqueous sodium bicarbonate solution and once with water. The organic phase was dried and concentrated. The crude product was purified by silica gel column chromatography using cyclohexane/methyl tert-butyl ether 1:2. This gave 0.56 g of the desired product as white crystals of m.p. 177-180° C.

Example 2

N-(3'-chloro-4'-fluorobiphenyl-2-yl)-3-fluoromethyl-1-methyl-1H-pyrazole-4-carboxamide At room temperature, 0.27 g of 3-fluoromethyl-1-methyl-1H-pyrazole-4-carbonyl chloride was added dropwise to a solution of 0.33 g of 3'-chloro-4'-fluoro-2-aminobiphenyl and 0.18 g of pyridine in 10 ml of toluene, and the mixture was stirred at room temperature for 16 hours. 10 ml of tetrahydrofuran and 30 ml of methyl tert-butyl ether were added, and the organic phase was washed successively with 2% strength hydrochloric acid, twice with 2% strength aqueous sodium hydroxide solution and then with dilute aqueous sodium chloride solution. The organic phase was dried and concentrated under reduced pressure. The crude product was triturated with 10 ml of diisopropyl ether and the solid that remained was filtered off with suction and dried. This gave 0.46 g of the desired product as a white powder of m.p. 133-134° C.

Example 3

N-(3',4'-dichlorobiphenyl-2-yl)methyl-1-methyl-3-trifluoromethyl-1H-pyrazole-4-carboxamide With ice cooling, 0.25 g of N-(3',4'-dichlorobiphenyl-2-yl)-1-methyl-3-trifluoromethyl-1H-pyrazole-4-carboxamide and 0.09 g of methyl iodide were added to a solution of 0.02 g of sodium hydride in 5 ml of N,N-dimethylformamide. The mixture was stirred at room temperature for 12 hours, and 1% strength hydrochloric acid and methyl tert-butyl ether were then added. The organic phase was washed successively with water and saturated aqueous sodium chloride solution, and the solution was concentrated under reduced pressure. The crude product was purified by silica gel column chromatography using cyclohexane/ethyl acetate 1:1. This gave 0.15 g of the desired product as a milk-like oil.

Example 4

N-(3',4'-dichlorobiphenyl-2-yl)-3-(dichlorofluoromethyl)-1-methyl-1H-pyrazole-4-carboxamide a) N-(3',4-Dichlorobiphenyl-2-yl)-3-(dichlorofluoromethyl)-1-methyl-1H-pyrazole-4-carboxamide 0.37 g of the oil from 4b was added dropwise to a solution of 0.36 g of 3',4'-dichloro-2-aminobiphenyl and 0.18 g of pyridine in 10 ml of toluene, and the reaction mixture was stirred at room temperature for 16 hours. 10 ml of tetrahydrofuran and 30 ml of methyl tert-butyl ether were then added. The organic phase was washed successively with 2% strength hydrochloric acid, twice with aqueous sodium bicarbonate solution and with dilute aqueous sodium chloride solution. The organic phase was dried and concentrated under reduced pressure. The crude product was triturated with 10 ml of diisopropyl ether, and the solid that remained was filtered off with suction and dried. This gave 0.48 g of the desired product as a white powder of m.p. 145-146° C.

b) 3-Dichlorofluoromethyl-1-methyl-4-pyrazolecarbonyl chloride

A mixture of 5.3 g of 3-dichlorofluoromethyl-1-methyl-4-pyrazolecarboxylic acid and 27.8 g of thionyl chloride was heated at reflux for 2 hours. The reaction mixture was then concentrated using a rotary evaporator and twice codistilled with 50 ml of toluene. The isolated oil was directly reacted further, without further purification.

c) 3-Dichlorofluoromethyl-1-methyl-4-pyrazolecarboxylic acid

At room temperature, a solution of 10.20 g of ethyl 3-dichlorofluoromethyl-1-methyl-4-carboxylate in 20 ml of tetrahydrofuran was added dropwise to a mixture of 5.13 g of potassium trimethylsilanolate and 100 ml of tetrahydrofuran, and the mixture was stirred at room temperature for 12 hours. The precipitate was filtered off with suction, washed with tetrahydrofuran and dried under reduced pressure. The resulting solid was dissolved in 200 ml of ice-water, and the solution was adjusted to pH 2 using 10% strength hydrochloric acid. The precipitate was extracted twice with methyl tert-butyl ether, and the combined organic phases were washed with saturated aqueous sodium chloride solution. After drying and evaporation of the solvent under reduced pressure, 5.50 g of the above acid were isolated as a white powder of m.p. 167-169° C.

The compounds of the general formula I where W=O listed in Table 9 below were prepared using the procedures given here.

TABLE 9

| Example | $R^1$ | $R^2$ | $R^3$ | $X^1$ | n | $X^2$ | m | Y | p | Characterization (m.p. or $^1$H NMR) |
|---|---|---|---|---|---|---|---|---|---|---|
| 9.1 | $CH_3$ | Cl | H | — | 0 | 3,4-$Cl_2$ | 2 | — | 0 | 104-108° C. |
| 9.2 | $CH_3$ | Cl | H | — | 0 | 2,4-$Cl_2$ | 2 | — | 0 | 117-122° C. |
| 9.3 | $CH_3$ | Cl | H | — | 0 | 3-Cl, 4-F | 2 | — | 0 | 134-137° C. |
| 9.4 | $CH_3$ | Cl | H | — | 0 | 3,5-$Cl_2$ | 2 | — | 0 | 135-139° C. |
| 9.5 | $CF_3$ | H | H | — | 0 | 2-F, 4-Cl | 2 | 5-$OCH_3$ | 1 | 119-121° C. |
| 9.6 | $CF_3$ | H | H | — | 0 | 2-F, 4-Cl | 2 | 5-$CH_3$ | 1 | 106-108° C. |
| 9.7 | $CF_3$ | H | H | — | 0 | 3,4,5-$F_3$ | 3 | — | 0 | 120-124° C. |
| 9.8 | $CF_3$ | H | H | — | 0 | 2,4,5-$F_3$ | 3 | — | 0 | 110-113° C. |
| 9.9 | $CHF_2$ | H | H | — | 0 | 2-F, 4-Cl | 2 | 5-$OCH_3$ | 1 | 150-152° C. |
| 9.10 | $CF_3$ | H | H | — | 0 | 2,3,4-$F_3$ | 3 | — | 0 | 123-125° C. |
| 9.11 | $CHF_2$ | H | H | — | 0 | 2-F, 4-Cl | 2 | 5-$CH_3$ | 1 | 120-122° C. |
| 9.12 | $CHF_2$ | H | H | — | 0 | 3,4,5-$F_3$ | 3 | — | 0 | 113-116° C. |
| 9.13 | $CHF_2$ | H | H | — | 0 | 2,4,5-$F_3$ | 3 | — | 0 | $^1$H-NMR (CDCl$_3$): δ = 8.20 (d, 1H), 7.95 (s, 1H), 7.80 (br s, 1H), 7.45 (m, 1H), 7.25 (m, 2H), 7.15 (m, 1H), 7.00 (m, 1H), 6.62 (t, 1H), 3.90 (s, 3H) |
| 9.14 | $CH_3$ | H | H | — | 0 | 3,4-$Cl_2$ | 2 | — | 0 | $^1$H-NMR (CDCl$_3$): δ = 8.40 (d, 1H), 7.60 (m, 2H), 7.45 (m, 1H), 7.25 (m, 5H), 3.85 (s, 3H), 2.20 (s, 3H) |
| 9.15 | $CH_3$ | H | H | — | 0 | 2,4-$Cl_2$ | 2 | — | 0 | $^1$H-NMR (CDCl$_3$): δ = 8.35 (d, 1H), 7.65 (s, 1H), 7.60 (s, 1H), 7.45 (m, 1H), 7.25 (m, 5H), 3.90 (s, 3H), 2.10 (s, 3H) |
| 9.16 | $CH_3$ | H | H | — | 0 | 3,4-$F_2$ | 2 | — | 0 | 140-143° C. |
| 9.17 | $CH_3$ | H | H | — | 0 | 3-Cl, 4-F | 2 | — | 0 | 177-180° C. |
| 9.18 | $CH_3$ | H | H | — | 0 | 3,5-$Cl_2$ | 2 | — | 0 | $^1$H-NMR (CDCl$_3$): δ = 8.40 (d, 1H), 7.60 (s, 1H), 7.45 (m, 2H), 7.35 (m, 2H), 7.25 (m, 3H), 3.92 (s, 3H), 2.20 (s, 3H) |
| 9.19 | $CH_3$ | H | H | — | 0 | 3-F, 4-Cl | 2 | — | 0 | 181-186° C. |
| 9.20 | $CH_3$ | H | H | — | 0 | 2,4-$F_2$ | 2 | — | 0 | $^1$H-NMR (CDCl$_3$): δ = 8.30 (d, 1H), 7.60 (s, 1H), 7.45 (m, 1H), 7.35 (m, 1H), 7.20 (m, 4H), 7.00 (m, 1H), 3.92 (s, 3H), 2.18 (s, 3H) |
| 9.21 | $CH_3$ | H | H | — | 0 | 2-F, 4-Cl | 2 | — | 0 | 122-125° C. |
| 9.22 | $CF_3$ | H | H | 3-Cl, 5-F | 2 | 2,4-$Cl_2$ | 2 | — | 0 | $^1$H-NMR (CDCl$_3$): δ = 7.95 (s, 2H), 7.85 (s, 1H), 7.40 (m, 2H), 7.25 (m, 2H), 3.95 (s, 3H) |
| 9.23 | $CHF_2$ | H | H | 3-Cl, 5-F | 2 | 3,4-$Cl_2$ | 2 | — | 0 | 147-152° C. |

TABLE 9-continued

| Example | $R^1$ | $R^2$ | $R^3$ | $X^1$ | n | $X^2$ | m | Y | p | Characterization (m.p. or $^1$H NMR) |
|---|---|---|---|---|---|---|---|---|---|---|
| 9.24 | $CHF_2$ | H | H | 3-Cl, 5-F | 2 | $3,4-F_2$ | 2 | — | 0 | $^1$H-NMR (DMSO-$d_6$): δ = 9.35 (s, 1H), 8.15 (s, 1H), 7.40-7.00 (m, 6H), 3.95 (s, 3H) |
| 9.25 | $CF_2Cl$ | H | H | — | 0 | $3,4-Cl_2$ | 2 | — | 0 | 131-133° C. |
| 9.26 | $CF_2Cl$ | H | H | — | 0 | 3-Cl, 4-F | 2 | — | 0 | 120-121° C. |
| 9.27 | $CF_2Cl$ | H | H | — | 0 | $3,4-F_2$ | 2 | — | 0 | 138-139° C. |
| 9.28 | $CF_2Cl$ | H | H | — | 0 | $3,5-Cl_2$ | 2 | — | 0 | 118-119° C. |
| 9.29 | $CF_2Cl$ | H | H | — | 0 | $2,4-Cl_2$ | 2 | — | 0 | 126-127° C. |
| 9.30 | $CF_3$ | F | H | — | 0 | 3-Cl, 4-F | 2 | — | 0 | 159-160° C. |
| 9.31 | $CF_3$ | F | H | — | 0 | $3,5-Cl_2$ | 2 | — | 0 | 158-159° C. |
| 9.32 | $CF_3$ | F | H | — | 0 | $2,4-Cl_2$ | 2 | — | 0 | 132-134° C. |
| 9.33 | $CF_3$ | F | H | — | 0 | $3,4-Cl_2$ | 2 | — | 0 | 148-150° C. |
| 9.34 | $CF_3$ | H | $CH_3$ | — | 0 | 3-Cl, 4-F | 2 | — | 0 | $^1$H-NMR (CDCl$_3$): δ = 7.50-7.20 (m, 4H), 7.15 (m, 1H), 7.05 (m, 1H), 6.95 (m, 1H), 6.25 (s, 1H), 3.65 (s, 3H), 3.30 (s, 3H) |
| 9.35 | $CF_3$ | H | $CH_3$ | — | 0 | $3,4-Cl_2$ | 2 | — | 0 | $^1$H-NMR (CDCl$_3$): δ = 7.50-7.15 (m, 5H), 7.05 (s, 1H), 6.90 (d, 1H), 6.25 (s, 1H), 3.65 (s, 3H), 3.25 (s, 3H) |
| 9.36 | $CF_3$ | H | $CH_2CH_3$ | — | 0 | $3,4-Cl_2$ | 2 | — | 0 | $^1$H-NMR (CDCl$_3$): δ = 7.50-7.15 (m, 6H), 7.00 (d, 1H), 6.25 (s, 1H), 4.20 (m, 1H), 3.00 (m, 1H), 1.20 (m, 3H) |
| 9.37 | CHFCl | H | H | — | 0 | $3,4-Cl_2$ | 2 | — | 0 | 122-124° C. |
| 9.38 | CHFCl | H | H | — | 0 | 3-Cl, 4-F | 2 | — | 0 | 85-87° C. |
| 9.39 | CHFCl | H | H | — | 0 | $3,4-F_2$ | 2 | — | 0 | 137-138° C. |
| 9.40 | CHFCl | H | H | — | 0 | $3,5-Cl_2$ | 2 | — | 0 | 100-102° C. |
| 9.41 | CHFCl | H | H | — | 0 | $2,4-Cl_2$ | 2 | — | 0 | 142-144° C. |
| 9.42 | $CH_2F$ | H | H | — | 0 | $3,4-Cl_2$ | 2 | — | 0 | 134-136° C. |
| 9.43 | $CH_2F$ | H | H | — | 0 | 3-Cl, 4-F | 2 | — | 0 | 133-134° C. |
| 9.44 | $CH_2F$ | H | H | — | 0 | $3,4-F_2$ | 2 | — | 0 | 141-143° C. |
| 9.45 | $CH_2F$ | H | H | — | 0 | $3,5-Cl_2$ | 2 | — | 0 | 135-137° C. |
| 9.46 | $CH_2F$ | H | H | — | 0 | $2,4-Cl_2$ | 2 | — | 0 | 111-112° C. |
| 9.47 | $CFCl_2$ | H | H | — | 0 | $3,4-Cl_2$ | 2 | — | 0 | 145-146° C. |
| 9.48 | $CFCl_2$ | H | H | — | 0 | 3-Cl, 4-F | 2 | — | 0 | 70-71° C. |
| 9.49 | $CFCl_2$ | H | H | — | 0 | $3,4-F_2$ | 2 | — | 0 | 123-124° C. |
| 9.50 | $CFCl_2$ | H | H | — | 0 | $3,5-Cl_2$ | 2 | — | 0 | 107-108° C. |
| 9.51 | $CFCl_2$ | H | H | — | 0 | $2,4-Cl_2$ | 2 | — | 0 | 121-123° C. |
| 9.52 | $CH_2F$ | H | H | — | 0 | $3,4,5-F_3$ | 3 | — | 0 | 152-156° C. |
| 9.53 | $CH_2Cl$ | H | H | — | 0 | $3,4,5-F_3$ | 3 | — | 0 | 158-161° C. |
| 9.54 | CHFCl | H | H | — | 0 | $3,4,5-F_3$ | 3 | — | 0 | 154-157° C. |
| 9.55 | $CH_2F$ | H | H | — | 0 | 3-F, 4-Cl | 2 | — | 0 | 172-174° C. |
| 9.56 | $CH_2F$ | H | H | — | 0 | 2-F, 4-Cl | 2 | — | 0 | 111-114° C. |
| 9.57 | $CH_2F$ | H | H | — | 0 | $2,3,4-F_3$ | 3 | — | 0 | 126-129° C. |
| 9.58 | $CH_2F$ | H | H | — | 0 | $2,4,5-F_3$ | 3 | — | 0 | 133-136° C. |
| 9.59 | $CH_2F$ | H | H | — | 0 | $2,4-F_2$ | 2 | — | 0 | 100-102° C. |
| 9.60 | $CH_2F$ | H | H | — | 0 | 2-Cl, 4-F | 2 | — | 0 | 104-106° C. |
| 9.61 | $CH_2F$ | H | H | — | 0 | $3,5-F_2$ | 2 | — | 0 | 111-115° C. |

Use Examples

The fungicidal action of the compounds I according to the invention was demonstrated by the following tests:

The active compounds were prepared as a stock solution comprising 25 mg of active compound which was made up to 10 ml using a mixture of acetone and/or dimethyl sulfoxide and the emulsifier Uniperol® EL (wetting agent having an emulsifying and dispersing action based on ethoxylated alkylphenols) in a volume ratio of solvent/emulsifier of 99:1. The mixture was then made up to 100 ml with water. This stock solution was diluted with the solvent/emulsifier/water mixture described to give the desired concentration of active compounds.

Activity Against Gray Mold on Bell Pepper Leaves Caused by *Botrytis cinerea*, Protective Application Bell pepper seedlings of the cultivar "Neusiedler Ideal Elite" were, after 2-3 leaves were well developed, sprayed to runoff point with an aqueous suspension having the concentration of active compounds stated below. The next day, the treated plants were inoculated with a spore suspension of *Botrytis cinerea* which comprised $1.7\times10^6$ spores/ml in a 2% strength aqueous biomalt solution. The test plants were then placed into a dark climatized chamber at 22-24° C. and high atmospheric humidity. After 5 days, the extent of the fungal infection on the leaves could be determined visually in %.

In this test, the plants which had been treated with 250 mg/l of compounds 9.1, 9.3, 9.12, 9.13, 9.14, 9.17, 9.18, 9.19, 9.20, 9.30, 9.32, 9.33, 9.35, 9.36, 9.37, 9.38, 9.39, 9.40, 9.42, 9.43, 9.44 and 9.45 from Table 9 showed an infection of at most 20%, whereas the untreated plants were 90% infected.

Activity Against Leaf Blotch on Wheat Caused by *Leptosphaeria nodorum*

Pots of wheat plants of the cultivar "Kanzler" were sprayed to runoff point with an aqueous suspension having the concentration of active compounds stated below. The next day, the pots were inoculated with an aqueous spore suspension of *Leptosphaeria nodorum* (syn. *Stagonosporoa nodorum*, *Septoroia nodorum*). The plants were then placed into a chamber at 20° C. and maximum atmospheric humidity. After 8 days, the leaf blotch on the untreated but infected control plants had developed to such an extent that the infection could be determined visually in %.

In this test, the plants which had been treated with 250 mg/l of compounds 9.1, 9.2, 9.13 and 9.27 from Table 9 showed an infection of at most 20%, whereas the untreated plants were 60% infected.

Curative Activity Against Brown Rust on Wheat Caused by *Puccinia recondita*

Leaves of potted wheat seedlings of the cultivar "Kanzler" were inoculated with a spore suspension of brown rust (*Puccinia recondita*). The pots were then placed into a chamber with high atmospheric humidity (90 to 95%) at 20-22° C. for 24 hours. During this time, the spores germinated and the germ tubes penetrated into the leaf tissue. The next day, the infected plants were sprayed to runoff point with an aqueous suspension having the concentration of active compounds stated below. The suspension or emulsion was prepared as described above. After the spray coating had dried on, the test plants were cultivated in a greenhouse at temperatures between 20 and 22° C. and at 65 to 70% relative atmospheric humidity for 7 days. The extent of the rust fungus development on the leaves was then determined.

In this test, the plants which had been treated with 250 mg/l of compounds 9.1, 9.3, 9.4, 9.5, 9.6, 9.7, 9.8, 9.9, 9.10, 9.11, 9.12, 9.13, 9.14, 9.15, 9.17, 9.18, 9.19, 9.20, 9.21, 9.25, 9.26, 9.27, 9.28, 9.29, 9.33, 9.34, 9.35, 9.36, 9.37, 9.38, 9.39, 9.40, 9.42, 9.43, 9.44 and 9.45 from Table 9 showed an infection of at most 20%, whereas the untreated plants were 90% infected.

Comparative Experiment—Activity Against Gray Mold on Bell Pepper Leaves Caused by *Botrytis cinerea*, Protective Application Compound No. 47 of Table 1 from EP-A 0 589 301 was compared to compounds 9.17 and 9.20 according to the invention from Table 9.

Bell pepper seedlings of the cultivar "Neusiedler Ideal Elite" were, after 2-3 leaves were well developed, sprayed to runoff point with an aqueous suspension having the concentration of active compounds stated below. The next day, the treated plants were inoculated with a spore suspension of *Botrytis cinerea* which comprised $1.7\times10^6$ spores/ml in a 2% strength aqueous biomalt solution. The test plants were then placed into a dark climatized chamber at 22-24° C. and high atmospheric humidity. After 5 days, the extent of the fungal infection on the leaves could be determined visually in %.

TABLE 10

| Compound | Structure | Infection in % at 250 ppm at BOTRCI P1 |
|---|---|---|
| Comp. 47 | 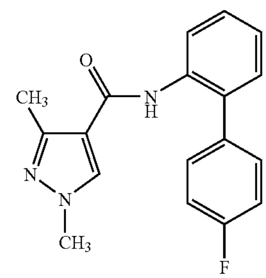 | 60 |
| 9.17 | 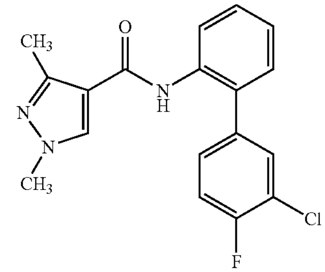 | 5 |
| 9.20 | 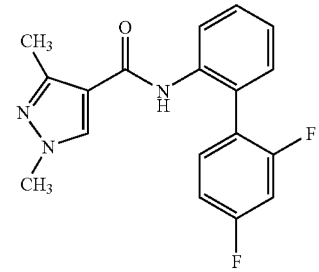 | 7 |
| untreated | | 90 |

As can be seen from the biological data of Table 10, the compounds 9.17 and 9.20 according to the invention clearly have improved fungicidal action compared to the structurally most similar compound of the prior art.

We claim:

1. A pyrazolecarboxanilide of the formula I

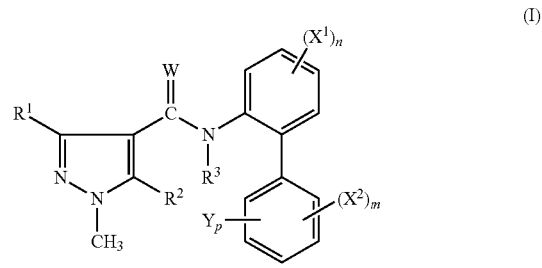

(I)

in which the variables are as defined below:
n is zero;
m is 3;
$X^2$ is halogen, where the radicals $X^2$ may have different meanings;
p is zero;
$R^1$ is $C_1$-$C_4$-haloalkyl;
$R^2$ is hydrogen or halogen;
$R^3$ is hydrogen; and
W is O.

2. The pyrazolecarboxanilide of the formula I according to claim 1 in which the variables are as defined below:
$X^2$ is fluorine or chlorine;
$R^1$ is fluoromethyl, difluoromethyl, chlorofluoromethyl, chlorodifluoromethyl, dichlorofluoromethyl or trifluoromethyl; and
$R^2$ is hydrogen, fluorine or chlorine.

3. The pyrazolecarboxanilide of the formula I according to claim 1 in which the variables are as defined below:
$X^2$ is fluorine or chlorine,
$R^1$ is fluoromethyl, difluoromethyl, chlorofluoromethyl, chlorodifluoromethyl, dichlorofluoromethyl or trifluoromethyl; and
$R^2$ is hydrogen or chlorine.

4. The pyrazolecarboxanilide of the formula I according to claim 1, selected from the group consisting of:
N-(3',4',5'-trifluorobiphenyl-2-yl)-1-methyl-3-trifluoromethyl-1H-pyrazole-4-carboxamide,
N-(2',4',5'-trifluorobiphenyl-2-yl)-1-methyl-3-trifluoromethyl-1H-pyrazole-4-carboxamide,
N-(2',3',4'-trifluorobiphenyl-2-yl)-1-methyl-3-trifluoromethyl-1H-pyrazole-4-carboxamide,
N-(3',4',5'-trifluorobiphenyl-2-yl)-1-methyl-3-difluoromethyl-1H-pyrazole-4-carboxamide,
N-(2',4',5'-trifluorobiphenyl-2-yl)-1-methyl-3-difluoromethyl-1H-pyrazole-4-carboxamide,
N-(3',4',5'-trifluorobiphenyl-2-yl)-1-methyl-3-chlorodifluoromethyl-1H-pyrazole-4-carboxamide,
N-(3',4',5'-trifluorobiphenyl-2-yl)-1-methyl-3-chlorofluoromethyl-1H-pyrazole-4-carboxamide,
N-(3',4',5'-trifluorobiphenyl-2-yl)-1-methyl-3-fluoromethyl-1H-pyrazole-4-carboxamide,
N-(2',3',4'-trifluorobiphenyl-2-yl)-1-methyl-3-fluoromethyl-1H-pyrazole-4-carboxamide, and
N-(2',4',5'-trifluorobiphenyl-2-yl)-1-methyl-3-fluoromethyl-1H-pyrazole-4-carboxamide.

5. A composition for controlling harmful fungi, which composition comprises a fungicidal amount of a compound of the formula I according to claim 1 and at least one inert additive.

6. The composition according to claim 5, additionally comprising a further active compound.

7. A method for controlling phytopathogenic harmful fungi, which comprises treating the harmful fungi, their habitat and/or the materials, plants, the soil or seed to be protected against fungal attack with a fungicidally effective amount of a compound of the formula I according to claim 1.

8. Seed, comprising a compound of the formula I according to claim 1 in an amount of from 1 to 1000 g/100 kg.

9. An aniline of the formula III

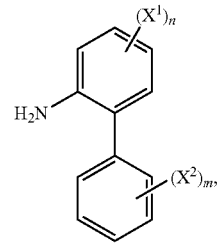

wherein the variables n, m, $X^1$ and $X^2$ have the meanings given in claim 1.

* * * * *